(12) United States Patent
Meyers et al.

(10) Patent No.: US 8,888,857 B2
(45) Date of Patent: *Nov. 18, 2014

(54) CONSTRAINED PROSTHETIC KNEE WITH ROTATING BEARING

(75) Inventors: John E. Meyers, Columbia City, IN (US); George D. Letson, Tampa, FL (US); Russell Windsor, Larchmont, NY (US); Vincent A. Webster, Warsaw, IN (US); Bill N. Sisk, Claypool, IN (US); Bill H. Haywood, Warsaw, IN (US); Adam M. Griner, Columbia City, IN (US); Michael Cook, Claypool, IN (US); Rodney L. Bays, Pierceton, IN (US); Jerry L. Aikins, Warsaw, IN (US); Marvin Figueroa, Warsaw, IN (US); Peter S. Walker, New York, NY (US)

(73) Assignee: Zimmer, Inc., Warsaw, IN (US)

( * ) Notice: Subject to any disclaimer, the term of this patent is extended or adjusted under 35 U.S.C. 154(b) by 7 days.

This patent is subject to a terminal disclaimer.

(21) Appl. No.: 13/603,899

(22) Filed: Sep. 5, 2012

(65) Prior Publication Data
US 2012/0330430 A1    Dec. 27, 2012

Related U.S. Application Data

(63) Continuation of application No. 12/790,181, filed on May 28, 2010, now Pat. No. 8,268,006, which is a
(Continued)

(51) Int. Cl.
*A61F 2/38* (2006.01)

(52) U.S. Cl.
CPC .............. *A61F 2/3868* (2013.01); *A61F 2/385* (2013.01)
USPC ....................................... 623/20.29

(58) Field of Classification Search
USPC ................. 623/20.14–20.35, 18.11
See application file for complete search history.

(56) References Cited

U.S. PATENT DOCUMENTS 1,504,903 A    8/1924    Rowley
2,183,076 A    12/1939   Kaiser
(Continued)

FOREIGN PATENT DOCUMENTS

BR    7506468 A     12/1975
CA    1073151 A1    3/1980
(Continued)

OTHER PUBLICATIONS

"U.S. Appl. No. 09/771,061, Non Final Office Action mailed Feb. 28, 2002", 8 pgs.
(Continued)

*Primary Examiner* — Alvin Stewart
(74) *Attorney, Agent, or Firm* — Schwegman Lundberg & Woessner, P.A.

(57) ABSTRACT

A constrained prosthetic knee having a modular hinge post and a rotating bearing. A cannulated hinge post is rotatably connected to the femoral component of the knee prosthesis so that a hinge post extension may be anteriorly positioned through the hinge post and into the tibial component of the knee prosthesis, after positioning of the femoral component in the femur and the tibial component in the tibia. The hinge post is preassembled to the femoral component so that such assembly is not required during the implantation procedure. A meniscal component forming the rotating bearing of the knee prosthesis is packaged together with the hinge post extension so that the appropriate hinge post extension is readily available. The meniscal component includes a mechanism for preventing lift off of the meniscal component from the tibial component, while allowing rotation of the meniscal component relative to the tibial component.

42 Claims, 12 Drawing Sheets

Related U.S. Application Data continuation of application No. 11/956,998, filed on Dec. 14, 2007, now abandoned, which is a continuation of application No. 10/805,056, filed on Mar. 19, 2004, now abandoned, which is a continuation of application No. 10/001,000, filed on Nov. 2, 2001, now Pat. No. 6,719,800, which is a continuation-in-part of application No. 09/771,061, filed on Jan. 29, 2001, now Pat. No. 6,485,519.

(56) References Cited

U.S. PATENT DOCUMENTS

| | | |
|---|---|---|
| 3,696,446 A | 10/1972 | Bousquet et al. |
| 3,708,805 A | 1/1973 | Scales et al. |
| 6,708,805 B2 | 1/1973 | Scales et al. |
| 3,813,700 A | 6/1974 | Tavernetti et al. |
| 3,816,853 A | 6/1974 | Elson |
| 3,824,630 A | 7/1974 | Johnston |
| 3,837,009 A | 9/1974 | Walker |
| 3,869,729 A | 3/1975 | Attenborough |
| 3,909,854 A | 10/1975 | Martinez |
| 3,918,101 A | 11/1975 | Lagrange et al. |
| 3,924,277 A | 12/1975 | Freeman et al. |
| 3,934,272 A | 1/1976 | Wearne et al. |
| 3,996,624 A | 12/1976 | Noiles |
| 4,016,606 A | 4/1977 | Murray et al. |
| 4,064,568 A | 12/1977 | Grundei et al. |
| 4,092,740 A | 6/1978 | Eshriqui |
| 4,094,017 A | 6/1978 | Matthews et al. |
| 4,112,522 A | 9/1978 | Dadurian et al. |
| 4,134,158 A | 1/1979 | Laure |
| 4,136,405 A | 1/1979 | Pastrick et al. |
| 4,215,439 A | 8/1980 | Gold |
| 4,216,549 A | 8/1980 | Hillberry et al. |
| 4,219,893 A | 9/1980 | Noiles |
| 4,224,697 A | 9/1980 | Murray et al. |
| 4,257,129 A | 3/1981 | Volz |
| 4,262,368 A | 4/1981 | Lacey |
| 4,268,920 A | 5/1981 | Engelbrecht et al. |
| 4,301,553 A | 11/1981 | Noiles |
| 4,340,978 A | 7/1982 | Buechel et al. |
| 4,358,859 A | 11/1982 | Schurman et al. |
| 4,383,337 A | 5/1983 | Volz et al. |
| 4,383,859 A | 5/1983 | Moore et al. |
| 4,404,691 A | 9/1983 | Buning et al. |
| 4,462,120 A | 7/1984 | Rambert et al. |
| 4,538,305 A | 9/1985 | Engelbrecht et al. |
| 4,578,081 A | 3/1986 | Harder et al. |
| 4,655,778 A | 4/1987 | Koeneman |
| 4,662,889 A | 5/1987 | Zichner et al. |
| 4,764,171 A | 8/1988 | Harder et al. |
| 4,790,853 A | 12/1988 | Engelbrecht et al. |
| 4,790,854 A | 12/1988 | Harder et al. |
| 4,822,366 A | 4/1989 | Bolesky |
| 4,828,564 A | 5/1989 | Scales et al. |
| 4,834,758 A | 5/1989 | Lane et al. |
| 4,865,606 A | 9/1989 | Rehder |
| 4,888,021 A | 12/1989 | Forte et al. |
| 4,919,660 A | 4/1990 | Peilloud |
| 4,923,472 A | 5/1990 | Ugolini |
| 4,936,853 A | 6/1990 | Fabian et al. |
| 4,938,769 A | 7/1990 | Shaw |
| 4,944,757 A | 7/1990 | Martinez et al. |
| 4,950,297 A | 8/1990 | Elloy et al. |
| 4,950,298 A | 8/1990 | Gustilo et al. |
| 5,007,933 A | 4/1991 | Sidebotham et al. |
| 5,011,496 A | 4/1991 | Forte et al. |
| 5,015,255 A | 5/1991 | Kuslich |
| 5,019,103 A | 5/1991 | Van Zile et al. |
| 5,037,439 A | 8/1991 | Albrektsson et al. |
| 5,061,271 A | 10/1991 | Van Zile |
| 5,116,375 A | 5/1992 | Hofmann |
| 5,123,928 A | 6/1992 | Moser |
| 5,139,521 A | 8/1992 | Schelhas |
| 5,171,283 A | 12/1992 | Pappas et al. |
| 5,180,383 A | 1/1993 | Haydon |
| 5,194,066 A | 3/1993 | Van Zile |
| 5,246,459 A | 9/1993 | Elias |
| 5,282,867 A | 2/1994 | Mikhail |
| 5,290,313 A | 3/1994 | Heldreth |
| 5,314,481 A | 5/1994 | Bianco |
| 5,326,368 A | 7/1994 | Collazo |
| 5,330,534 A | 7/1994 | Herrington et al. |
| 5,358,527 A | 10/1994 | Forte |
| 5,370,700 A | 12/1994 | Sarkisian et al. |
| 5,370,701 A * | 12/1994 | Finn ........................ 623/20.25 |
| 5,370,781 A | 12/1994 | Van De Wynckel et al. |
| 5,387,240 A | 2/1995 | Pottenger et al. |
| 5,395,401 A | 3/1995 | Bahler |
| 5,405,398 A | 4/1995 | Buford, III et al. |
| 5,411,555 A | 5/1995 | Nieder |
| 5,413,607 A | 5/1995 | Engelbrecht et al. |
| 5,427,586 A | 6/1995 | Schelhas |
| 5,458,644 A | 10/1995 | Grundei |
| 5,489,307 A | 2/1996 | Kuslich et al. |
| 5,489,311 A | 2/1996 | Cipolletti |
| 5,549,687 A | 8/1996 | Coates et al. |
| 5,549,689 A | 8/1996 | Epstein et al. |
| 5,609,639 A | 3/1997 | Walker |
| 5,609,643 A | 3/1997 | Colleran et al. |
| 5,658,342 A | 8/1997 | Draganich et al. |
| 5,683,468 A | 11/1997 | Pappas |
| 5,702,458 A | 12/1997 | Burstein et al. |
| 5,702,466 A | 12/1997 | Pappas et al. |
| 5,725,580 A | 3/1998 | Cloutier et al. |
| 5,755,804 A | 5/1998 | Schmotzer et al. |
| 5,766,257 A | 6/1998 | Goodman et al. |
| 5,772,661 A | 6/1998 | Michelson |
| 5,776,200 A | 7/1998 | Johnson et al. |
| 5,776,201 A | 7/1998 | Colleran et al. |
| 5,800,552 A | 9/1998 | Forte |
| 5,824,096 A | 10/1998 | Pappas et al. |
| 5,824,102 A | 10/1998 | Buscayret |
| 5,879,392 A | 3/1999 | McMinn |
| 5,879,394 A | 3/1999 | Ashby et al. |
| 5,906,643 A | 5/1999 | Walker |
| 5,954,770 A | 9/1999 | Schmotzer et al. |
| 5,964,808 A | 10/1999 | Blaha et al. |
| 6,004,352 A | 12/1999 | Buni |
| 6,013,103 A | 1/2000 | Kaufman et al. |
| 6,019,794 A | 2/2000 | Walker |
| 6,080,195 A | 6/2000 | Colleran et al. |
| 6,099,570 A | 8/2000 | Livet et al. |
| 6,099,571 A | 8/2000 | Knapp |
| 6,117,175 A | 9/2000 | Bosredon |
| 6,126,692 A | 10/2000 | Robie et al. |
| 6,143,034 A | 11/2000 | Burrows |
| 6,162,255 A | 12/2000 | Oyola |
| 6,171,342 B1 | 1/2001 | O'Neil et al. |
| 6,264,696 B1 | 7/2001 | Reigner et al. |
| 6,267,763 B1 | 7/2001 | Castro |
| 6,296,666 B1 | 10/2001 | Gardner |
| 6,299,646 B1 | 10/2001 | Chambat et al. |
| 6,306,171 B1 | 10/2001 | Conzemius |
| 6,306,172 B1 | 10/2001 | O'Neil et al. |
| 6,319,283 B1 | 11/2001 | Insall et al. |
| 6,361,564 B1 | 3/2002 | Marceaux et al. |
| 6,428,577 B1 | 8/2002 | Evans et al. |
| 6,436,145 B1 | 8/2002 | Miller |
| 6,443,991 B1 | 9/2002 | Running |
| 6,447,549 B1 | 9/2002 | Taft |
| 6,485,519 B2 * | 11/2002 | Meyers et al. ............. 623/20.24 |
| 6,491,726 B2 | 12/2002 | Pappas |
| 6,500,208 B1 | 12/2002 | Metzger et al. |
| 6,506,215 B1 | 1/2003 | Letot et al. |
| 6,620,198 B2 | 9/2003 | Burstein et al. |
| 6,629,999 B1 | 10/2003 | Serafin, Jr. |
| 6,652,588 B2 | 11/2003 | Hayes, Jr. et al. |
| 6,719,800 B2 * | 4/2004 | Meyers et al. ............. 623/20.24 |
| 6,743,258 B1 | 6/2004 | Keller |
| 6,755,864 B1 | 6/2004 | Brack et al. |
| 6,770,097 B2 | 8/2004 | Leclercq |
| 6,773,461 B2 | 8/2004 | Meyers et al. |

(56) References Cited

U.S. PATENT DOCUMENTS

| | | |
|---|---|---|
| 6,984,249 B2 | 1/2006 | Keller |
| 7,070,622 B1 | 7/2006 | Brown et al. |
| 7,172,628 B2 | 2/2007 | Lamprich et al. |
| 7,175,665 B2 | 2/2007 | German et al. |
| 7,232,465 B2 | 6/2007 | Keller |
| 7,326,252 B2 | 2/2008 | Otto et al. |
| 7,357,817 B2 | 4/2008 | D'Alessio, II |
| 7,569,054 B2 | 8/2009 | Michelson |
| 7,572,292 B2 | 8/2009 | Crabtree et al. |
| 7,591,855 B2 | 9/2009 | Keller |
| 7,658,767 B2 | 2/2010 | Wyss |
| 7,753,960 B2 | 7/2010 | Cipolletti et al. |
| 7,871,442 B2 | 1/2011 | Servidio |
| 8,268,006 B2 | 9/2012 | Meyers et al. |
| RE44,476 E * | 9/2013 | Meyers et al. ............ 623/20.24 |
| 2001/0003803 A1 | 6/2001 | Leclercq |
| 2001/0025199 A1 | 9/2001 | Rauscher |
| 2001/0034554 A1 | 10/2001 | Pappas |
| 2002/0103541 A1 | 8/2002 | Meyers et al. |
| 2002/0107576 A1 | 8/2002 | Meyers et al. |
| 2002/0161448 A1 | 10/2002 | Hayes, Jr. et al. |
| 2003/0009228 A1 | 1/2003 | Meyers et al. |
| 2003/0009232 A1 | 1/2003 | Metzger et al. |
| 2003/0153980 A1 | 8/2003 | Brack |
| 2004/0054416 A1 | 3/2004 | Wyss et al. |
| 2004/0162620 A1 | 8/2004 | Wyss |
| 2004/0186583 A1 | 9/2004 | Keller |
| 2004/0186584 A1 | 9/2004 | Keller |
| 2004/0220676 A1 | 11/2004 | Keller |
| 2004/0249467 A1 | 12/2004 | Meyers et al. |
| 2005/0107886 A1 | 5/2005 | Crabtree et al. |
| 2005/0192672 A1 | 9/2005 | Wyss et al. |
| 2005/0246028 A1 | 11/2005 | Pappas et al. |
| 2007/0100463 A1 | 5/2007 | Aram et al. |
| 2008/0004708 A1 | 1/2008 | Wyss |
| 2008/0097616 A1 | 4/2008 | Meyers et al. |
| 2008/0167722 A1 | 7/2008 | Metzger et al. |
| 2008/0255671 A1 | 10/2008 | Kriek |
| 2009/0024221 A1 | 1/2009 | Ball |
| 2009/0082873 A1 | 3/2009 | Hazebrouck et al. |
| 2009/0088860 A1 | 4/2009 | Romeis et al. |
| 2009/0125116 A1 | 5/2009 | Crabtree et al. |
| 2009/0149964 A1 | 6/2009 | May et al. |
| 2009/0299482 A1 | 12/2009 | Metzger et al. |
| 2009/0326665 A1 | 12/2009 | Wyss et al. |
| 2009/0326666 A1 | 12/2009 | Wyss et al. |
| 2010/0016978 A1 | 1/2010 | Williams et al. |
| 2010/0016979 A1 | 1/2010 | Donno et al. |
| 2010/0042224 A1 | 2/2010 | Otto et al. |
| 2010/0063594 A1 | 3/2010 | Hazebrouck et al. |
| 2010/0100189 A1 | 4/2010 | Metzger |
| 2010/0234962 A1 | 9/2010 | Meyers et al. |

FOREIGN PATENT DOCUMENTS

| | | | |
|---|---|---|---|
| CH | 555671 A | | 11/1974 |
| CH | 613111 A5 | | 9/1979 |
| DE | 2114287 A1 | | 9/1972 |
| DE | 2122390 A1 | | 1/1973 |
| DE | 2154338 A1 | | 5/1973 |
| DE | 2310343 A1 | | 9/1973 |
| DE | 2227090 A1 | | 12/1973 |
| DE | 2244064 A1 | | 3/1974 |
| DE | 2334265 A1 | | 1/1975 |
| DE | 2531080 A | | 2/1976 |
| DE | 2543911 A1 | | 4/1976 |
| DE | 2545821 A1 | | 4/1976 |
| DE | 2452412 A1 | | 5/1976 |
| DE | 2631351 A1 | | 2/1977 |
| DE | 2636816 A1 | | 2/1977 |
| DE | 2539717 A1 | | 3/1977 |
| DE | 2549819 A1 | | 5/1977 |
| DE | 2810748 A1 | | 11/1978 |
| DE | 2744710 A1 | | 4/1979 |
| DE | 2802568 A1 | | 7/1979 |
| DE | 2906458 A1 | | 8/1979 |
| DE | 3013155 A1 | | 10/1980 |
| DE | 3039992 A1 | | 5/1981 |
| DE | 3022668 A1 | | 12/1981 |
| DE | 3339102 A1 | | 5/1984 |
| DE | 3334531 A1 | | 8/1985 |
| DE | 3529894 A1 | | 3/1987 |
| DE | 4102509 A1 | | 7/1992 |
| DE | 4110048 C1 | | 7/1992 |
| DE | 9414970 U1 | | 12/1994 |
| DE | 4434806 A1 | | 4/1996 |
| DE | 69206397 T2 | | 8/1996 |
| DE | 19618321 A1 | | 8/1997 |
| DE | 69305434 T2 | | 11/1997 |
| DE | 19809041 A1 | | 9/1999 |
| DE | 19915053 A1 | | 10/1999 |
| DE | 69324016 T2 | | 10/1999 |
| DE | 10012059 A1 | | 9/2001 |
| DE | 69712258 T2 | | 3/2003 |
| EP | 0046924 A2 | | 3/1982 |
| EP | 0069683 A1 | | 1/1983 |
| EP | 0083155 A1 | | 7/1983 |
| EP | 0126978 A1 | | 12/1984 |
| EP | 0198163 A2 | | 2/1986 |
| EP | 0177755 A1 | | 4/1986 |
| EP | 0178445 A1 | | 4/1986 |
| EP | 0194326 A1 | | 9/1986 |
| EP | 0214773 A2 | | 3/1987 |
| EP | 0265325 A1 | | 4/1988 |
| EP | 0177755 B1 | | 11/1988 |
| EP | 0410237 A1 | | 1/1991 |
| EP | 0420460 A1 | | 4/1991 |
| EP | 0472475 A2 | | 2/1992 |
| EP | 0510299 A1 | | 10/1992 |
| EP | 0519873 A2 | | 12/1992 |
| EP | 0552950 A1 | | 7/1993 |
| EP | 553585 A2 | | 8/1993 |
| EP | 621019 A1 | | 10/1994 |
| EP | 0653194 B1 | | 5/1995 |
| EP | 0716839 A1 | | 6/1996 |
| EP | 0724868 A1 | | 8/1996 |
| EP | 0791343 A2 | | 8/1997 |
| EP | 0812582 A2 | | 12/1997 |
| EP | 0913132 A1 | | 5/1999 |
| EP | 0923916 A1 | | 6/1999 |
| EP | 1108403 A1 | | 6/2001 |
| EP | 1132064 A2 | | 9/2001 |
| EP | 1226800 A2 | | 7/2002 |
| EP | 1417938 A1 | | 5/2004 |
| EP | 1447060 A2 | | 8/2004 |
| EP | 1447060 A3 | | 3/2006 |
| FR | 1532997 A | | 7/1968 |
| FR | 2076838 A5 | | 10/1971 |
| FR | 2330375 A1 | | 6/1977 |
| FR | 2330377 A1 | | 6/1977 |
| FR | 2445137 A1 | | 7/1980 |
| FR | 2601873 A1 | | 1/1988 |
| FR | 2612767 A1 | | 9/1988 |
| FR | 2628316 A1 | | 9/1989 |
| FR | 2641966 A1 | | 7/1990 |
| FR | 2692475 A1 | | 12/1993 |
| FR | 2696926 A1 | | 4/1994 |
| FR | 2696927 A1 | | 4/1994 |
| FR | 2702651 A1 | | 9/1994 |
| FR | 2711750 A1 | | 5/1995 |
| FR | 2716618 A1 | | 9/1995 |
| FR | 2751204 A1 | | 1/1998 |
| FR | 2760352 A1 | | 9/1998 |
| FR | 2771283 A1 | | 5/1999 |
| FR | 2777453 A1 | | 10/1999 |
| FR | 2787992 A1 | | 7/2000 |
| FR | 2793676 A1 | | 11/2000 |
| FR | 2793677 A1 | | 11/2000 |
| GB | 1328497 A | | 8/1973 |
| GB | 1409150 A | | 10/1975 |
| GB | 1457147 A | | 12/1976 |
| GB | 1475688 A | | 6/1977 |
| GB | 1507309 A | | 4/1978 |

(56) References Cited

FOREIGN PATENT DOCUMENTS

| | | |
|---|---|---|
| GB | 1509366 A | 5/1978 |
| GB | 1514479 A | 6/1978 |
| GB | 2070939 A | 9/1981 |
| GB | 2120943 A | 12/1983 |
| GB | 2129306 A | 5/1984 |
| GB | 2276553 A | 10/1994 |
| JP | 5241775 A | 9/1993 |
| JP | 8173464 A | 7/1996 |
| JP | 10014935 A | 1/1998 |
| RU | 208084001 C1 | 6/1997 |
| WO | WO-8100606 A1 | 3/1981 |
| WO | WO-8906947 A1 | 8/1989 |
| WO | WO-9421198 A1 | 9/1994 |
| WO | WO-9913804 A1 | 3/1999 |
| WO | WO-0066043 A1 | 11/2000 |
| WO | WO-0100606 A1 | 4/2001 |

OTHER PUBLICATIONS

"U.S. Appl. No. 09/771,061, Notice of Allowance mailed Jun. 28, 2002", 3 pgs.

"U.S. Appl. No. 09/771,061, Response filed Jun. 6, 2002 to Non Final Office Action mailed Feb. 28, 2002", 8 pgs.

"U.S. Appl. No. 10/001,000, Non Final Office Action mailed May 2, 2003", 6 pgs.

"U.S. Appl. No. 10/001,000, Notice of Allowance mailed Aug. 11, 2003", 5 pgs.

"U.S. Appl. No. 10/001,000, Response filed Jul. 25, 2003 to Non Final Office Action mailed May 2, 2003", 15 pgs.

"U.S. Appl. No. 10/234,362, Non Final Office Action mailed Apr. 23, 2003", 6 pgs.

"U.S. Appl. No. 10/234,362, Notice of Allowance mailed Jan. 12, 2004", 5 pgs.

"U.S. Appl. No. 10/234,362, Preliminary Amendment filed Sep. 4, 2002", 6 pgs.

"U.S. Appl. No. 10/234,362, Response filed Jul. 22, 2003 to Non Final Office Action mailed Apr. 23, 2003", 11 pgs.

"U.S. Appl. No. 10/234,362, Supplemental Notice of Allowability mailed Jun. 23, 2004", 4 pgs.

"U.S. Appl. No. 10/805,056, Final Office Action mailed Jun. 15, 2007", 7 pgs.

"U.S. Appl. No. 10/805,056, Non Final Office Action mailed Jan. 2, 2007", 5 pgs.

"U.S. Appl. No. 10/805,056, Preliminary Amendment filed Mar. 19, 2004", 4 pgs.

"U.S. Appl. No. 10/805,056, Response filed Apr. 3, 2007 to Non Final Office Action mailed Jan. 3, 2007", 7 pgs.

"U.S. Appl. No. 11/956,998, Non Final Office Action mailed Dec. 1, 2009", 8 pgs.

"U.S. Appl. No. 11/956,998, Response filed Nov. 6, 2009 to Restriction Requirement mailed May 8, 2009", 1 pg.

"U.S. Appl. No. 11/956,998, Restriction Requirement mailed May 8, 2009", 5 pgs.

"U.S. Appl. No. 12/776,218, Final Office Action mailed Apr. 18, 2011", 8 pgs.

"U.S. Appl. No. 12/776,218, Final Office Action mailed Apr. 24, 2012", 9 pgs.

"U.S. Appl. No. 12/776,218, Non Final Office Action mailed Sep. 8, 2011", 9 pgs.

"U.S. Appl. No. 12/776,218, Non Final Office Action mailed Dec. 2, 2010", 8 pgs.

"U.S. Appl. No. 12/776,218, Preliminary Amendment filed May 7, 2010", 10 pgs.

"U.S. Appl. No. 12/776,218, Response filed Mar. 8, 2012 to Non Final Office Action mailed Sep. 8, 2011", 18 pgs.

"U.S. Appl. No. 12/776,218, Response filed Apr. 4, 2011 to Non Final Office Action mailed Dec. 2, 2010", 18 pgs.

"U.S. Appl. No. 12/776,218, Response filed Aug. 18, 2011 to Final Office Action mailed Apr. 18, 2011", 18 pgs.

"U.S. Appl. No. 12/776,221, Final Office Action mailed Apr. 18, 2011", 5 pgs.

"U.S. Appl. No. 12/776,221, Final Office Action mailed Apr. 24, 2012", 5 pgs.

"U.S. Appl. No. 12/776,221, Non Final Office Action mailed Oct. 28, 2011", 5 pgs.

"U.S. Appl. No. 12/776,221, Non Final Office Action mailed Nov. 19, 2010", 7 pgs.

"U.S. Appl. No. 12/776,221, Preliminary Amendment filed May 7, 2010", 10 pgs.

"U.S. Appl. No. 12/776,221, Response filed Mar. 28, 2012 to Non Final Office Action mailed Oct. 28, 2011", 15 pgs.

"U.S. Appl. No. 12/776,221, Response filed Apr. 4, 2011 to Non Final Office Action mailed Nov. 19, 2010", 14 pgs.

"U.S. Appl. No. 12/776,221, Response filed Oct. 18. 2011 to Final Office Action mailed Apr. 18. 2011", 12 pgs.

"U.S. Appl. No. 12/776,224, Final Office Action mailed Feb. 22, 2013", 4 pgs.

"U.S. Appl. No. 12/776,224, Final Office Action mailed Apr. 19, 2011", 5 pgs.

"U.S. Appl. No. 12/776,224, Final Office Action mailed Apr. 12, 2012", 6 pgs.

"U.S. Appl. No. 12/776,224, Non Final Office Action mailed Sep. 7, 2011", 6 pgs.

"U.S. Appl. No. 12/776,224, Non Final Office Action mailed Nov. 8, 2012", 7 pgs.

"U.S. Appl. No. 12/776,224, Non Final Office Action mailed Nov. 19, 2010", 5 pgs.

"U.S. Appl. No. 12/776,224, Notice of Allowance mailed Jul. 12, 2013", 7 pgs.

"U.S. Appl. No. 12/776,224, Preliminary Amendment filed May 7, 2010", 8 pgs.

"U.S. Appl. No. 12/776,224, Response filed Feb. 8, 2013 to Non Final Office Action mailed Nov. 8, 2012", 15 pgs.

"U.S. Appl. No. 12/776,224, Response filed Mar. 7, 2012 to Non Final Office Action mailed Sep. 7, 2011", 11 pgs.

"U.S. Appl. No. 12/776,224, Response filed Apr. 4, 2011 to Non Final Office Action mailed Nov. 19, 2010", 10 pgs.

"U.S. Appl. No. 12/776,224, Response filed May 22, 2013 to Final Office Action mailed Feb. 22, 2013", 10 pgs.

"U.S. Appl. No. 12/776,224, Response filed Aug. 19, 2011 to Final Office Action mailed Apr. 19, 2011", 9 pgs.

"U.S. Appl. No. 12/776,224, Response filed Sep. 24, 2012 to Final Office Action mailed Apr. 24, 2012", 14 pgs.

"U.S. Appl. No. 12/776,224, Supplemental Response filed Mar. 9, 2012 to Non Final Office Action mailed Sep. 7, 2011", 8 pgs.

"U.S. Appl. No. 12/790,181, 312 Amendment filed Oct. 19, 2011", 13 pgs.

"U.S. Appl. No. 12/790,181, Non Final Office Action mailed Mar. 3, 2011", 6 pgs.

"U.S. Appl. No. 12/790,181, Notice of Allowance mailed Jan. 26, 2012", 7 pgs.

"U.S. Appl. No. 12/790,181, Notice of Allowance mailed May 9, 2012", 7 pgs.

"U.S. Appl. No. 12/790,181, Notice of Allowance mailed Jun. 27, 11", 7 pgs.

"U.S. Appl. No. 12/790,181, Notice of Allowance mailed Aug. 3, 2011", 7 pgs.

"U.S. Appl. No. 12/790,181, Preliminary Amendment May 26, 2012", 13 pgs.

"U.S. Appl. No. 12/790,181, Preliminary Amendment filed May 28, 2010", 12 pgs.

"U.S. Appl. No. 12/790,181, Preliminary Amendment filed Jul. 15, 2011", 12 pgs.

"U.S. Appl. No. 12/790,181, PTO Response to 312 Amendment mailed Oct. 31, 2011", 2 pgs.

"U.S. Appl. No. 12/790,181, Response filed Apr. 4, 2011 to Non Final Office Action mailed Mar. 3, 2011", 15 pgs.

"Canada Application U.S. Appl. No. 2,367,652, Office Action mailed Mar. 2, 2009", 3 pgs.

(56) References Cited

OTHER PUBLICATIONS

"Canada Application U.S. Appl. No. 2,367,652, Response filed Sep. 2, 2009 to Office Action mailed Mar. 2, 2009", 9 pgs.

"European Application Serial No. 02250512.7, Office Action mailed Nov. 2, 2010", 2 pgs.

"European Application Serial No. 03255512.0, European Search Report mailed Dec. 5, 2004", 19 pgs.

"European Application Serial No. 03255512.0, Office Action mailed Sep. 26, 2007", 9 pgs.

"European Application Serial No. 04012041.2, European Search Report mailed Feb. 3, 2006", 6 pgs.

"European Application Serial No. 04012041.2, European Search Report mailed Mar. 22, 2006", 24 pgs.

"European Application Serial No. 04012041.2, Office Action mailed Jul. 3, 2007", 5 pgs.

"European Application Serial No. 10012581.4, European Search Report mailed Dec. 13, 2010", 2 pgs.

"European Application Serial No. 10012582.2, Amendment filed Sep. 30, 2010", 15 pgs.

"European Application Serial No. 10012582.2, European Search Report mailed Dec. 10, 2010", 2 pgs.

"European Application Serial No. 10012582.2, Response filed May 12, 2011 to Search Opinion mailed Dec. 20, 2010", 15 pgs.

* cited by examiner

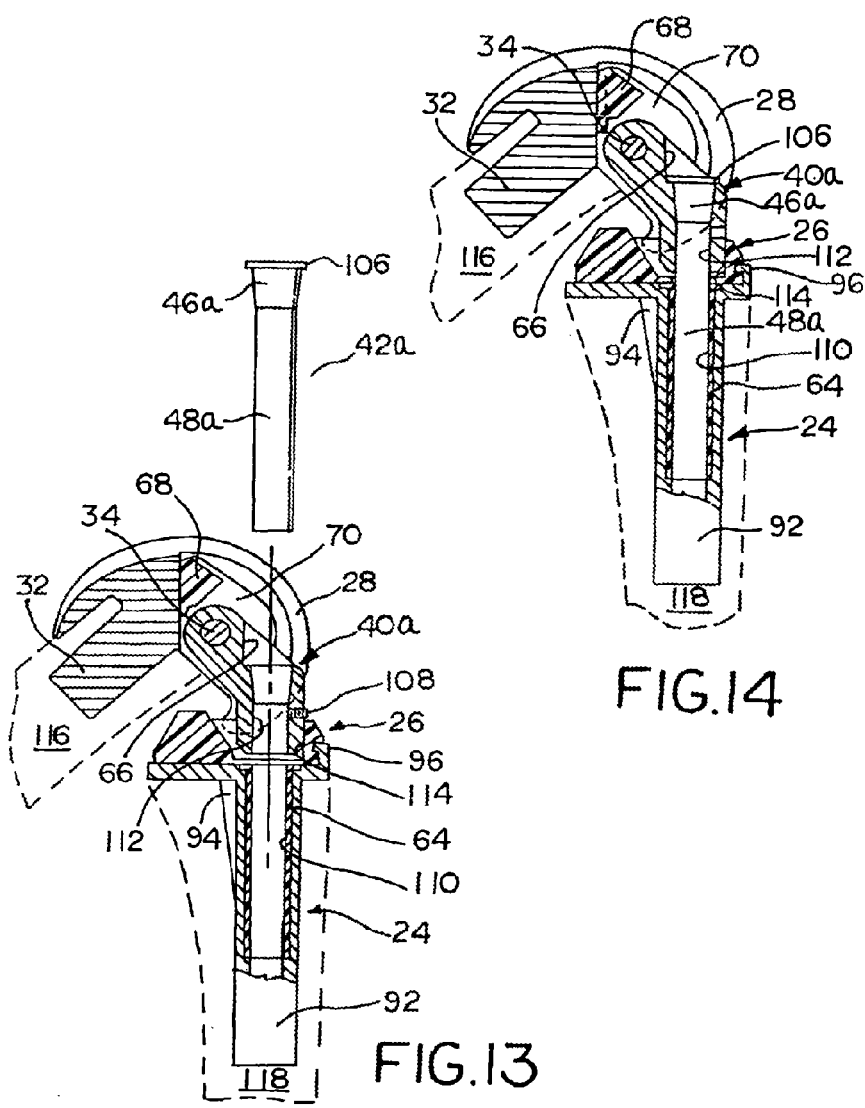

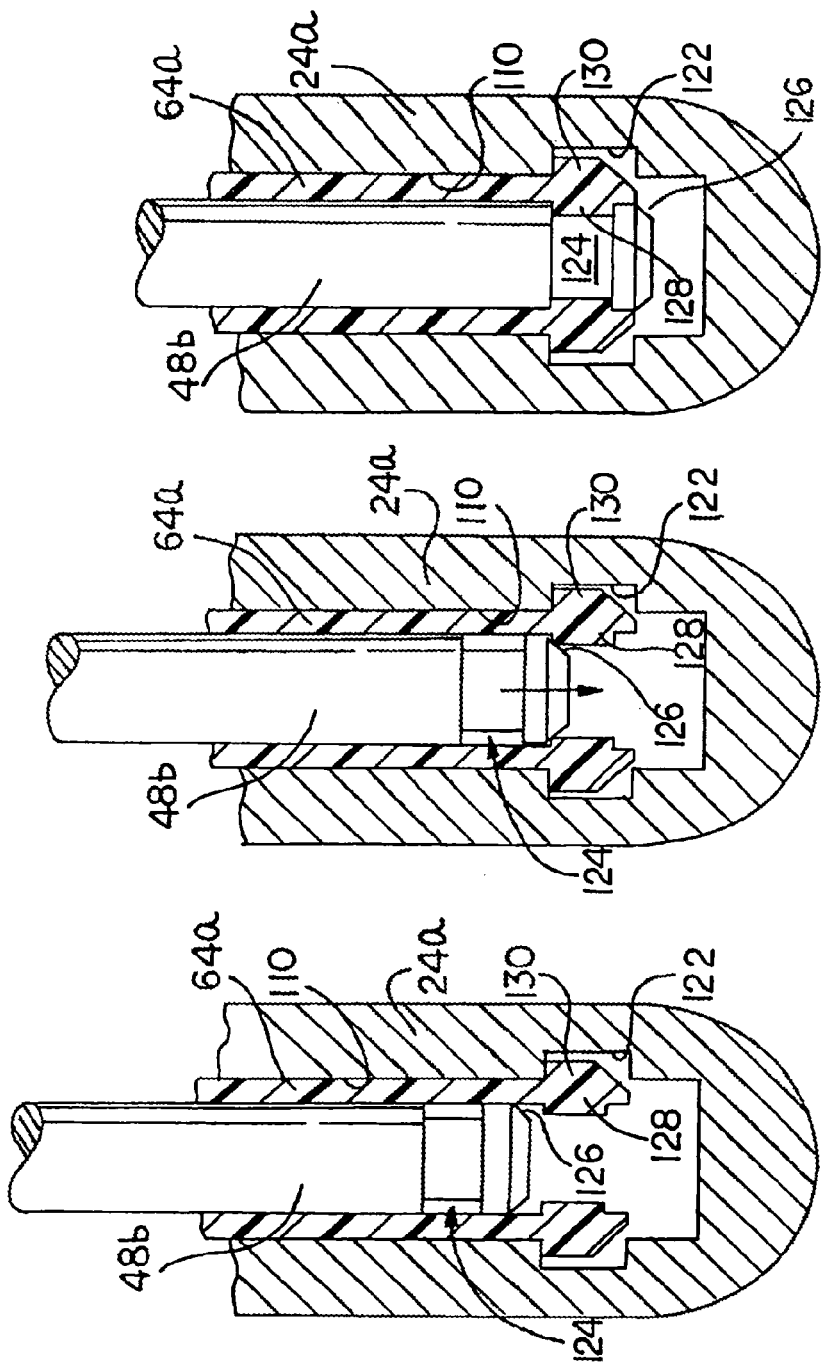

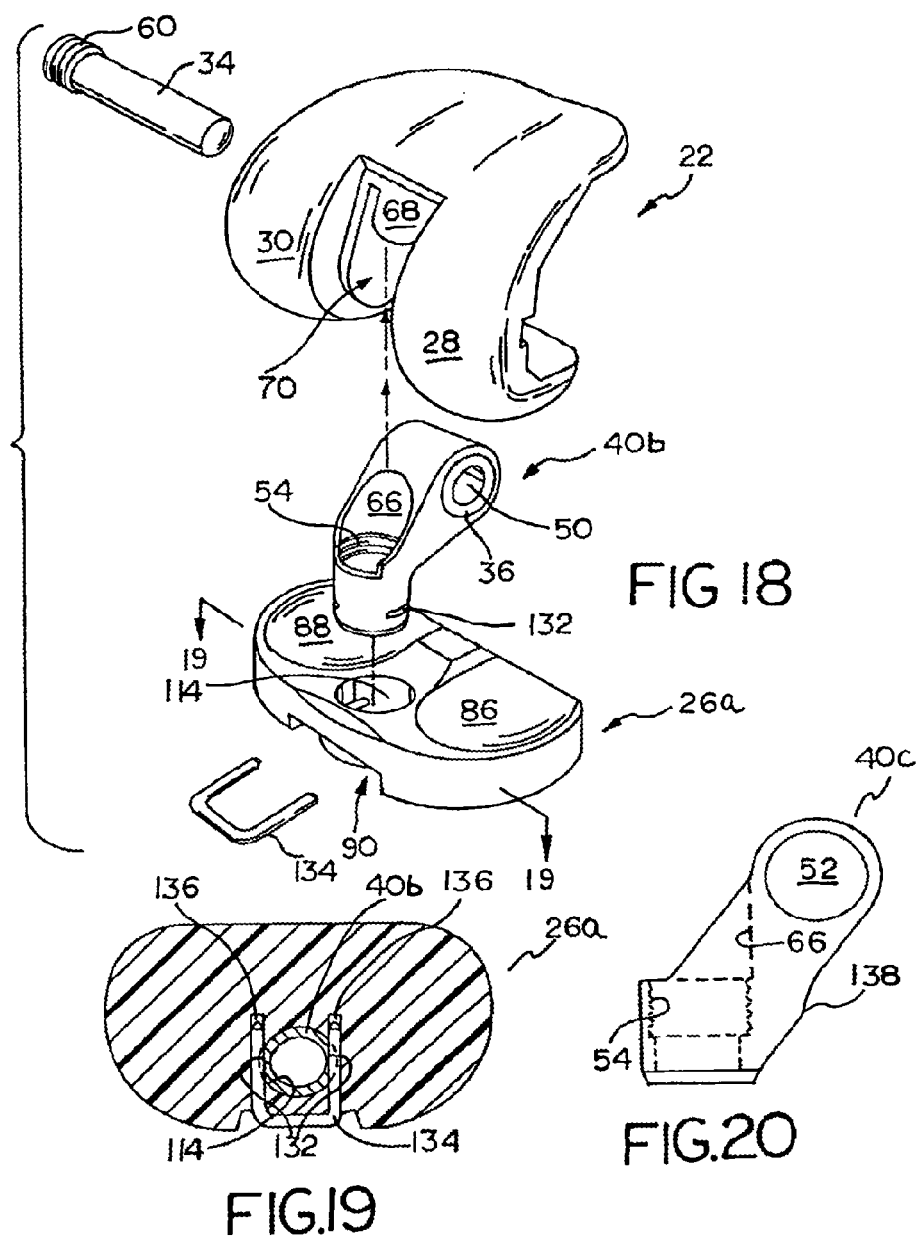

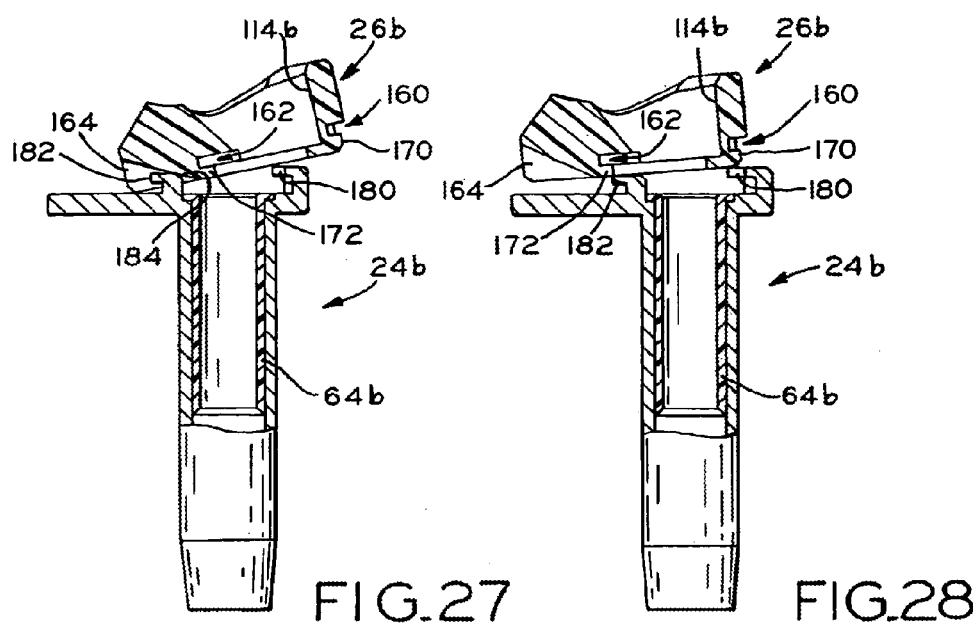
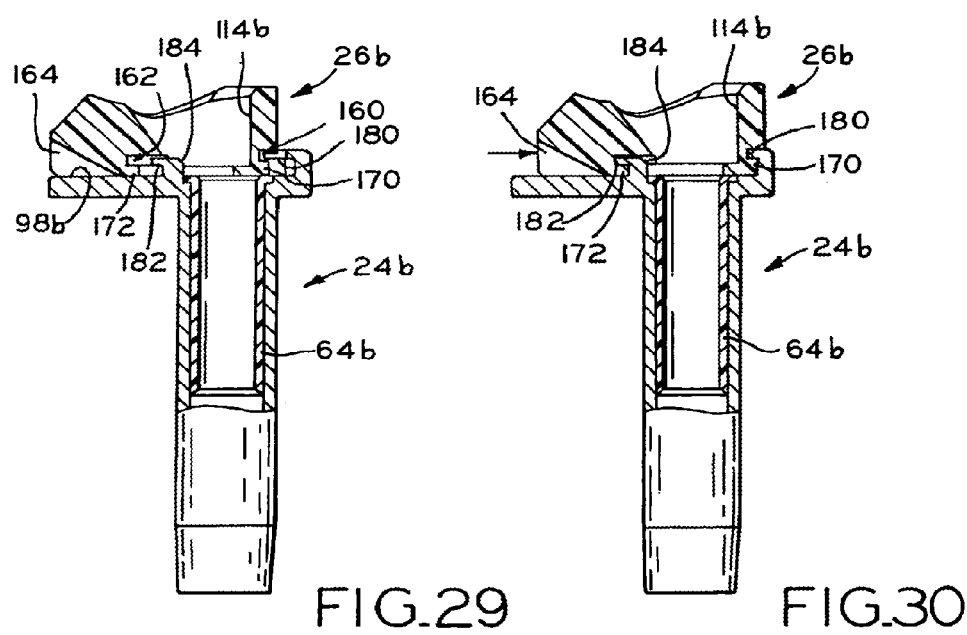

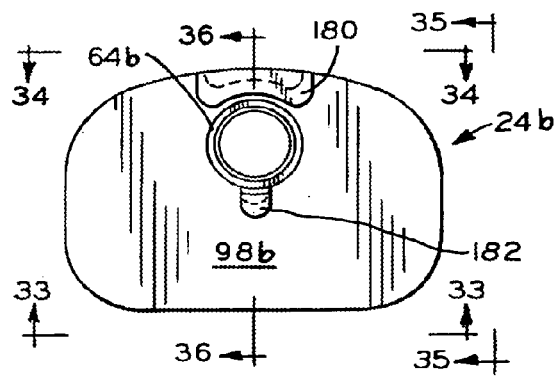
FIG_31
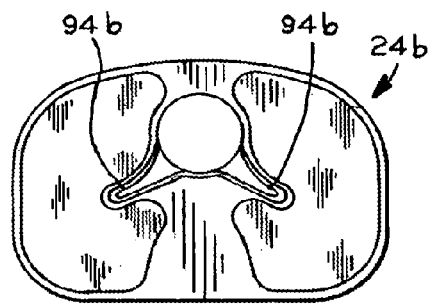
FIG_32
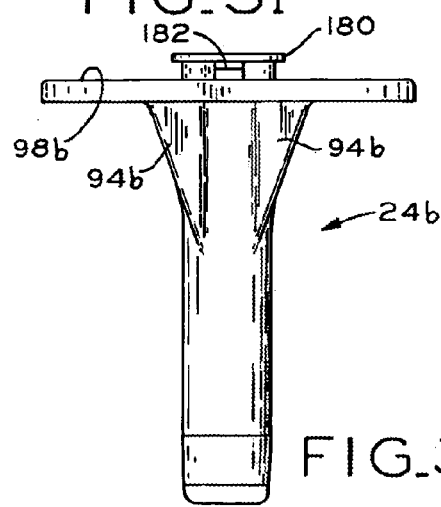
FIG_33
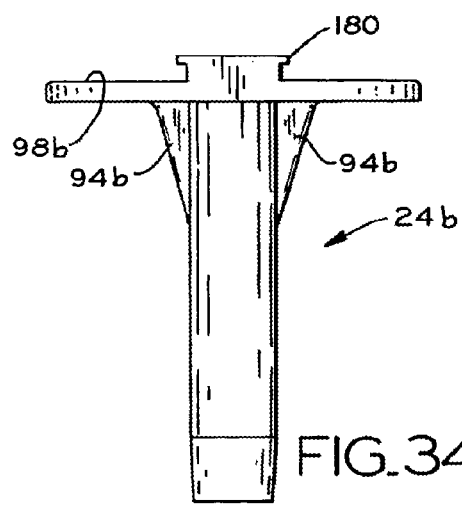
FIG_34
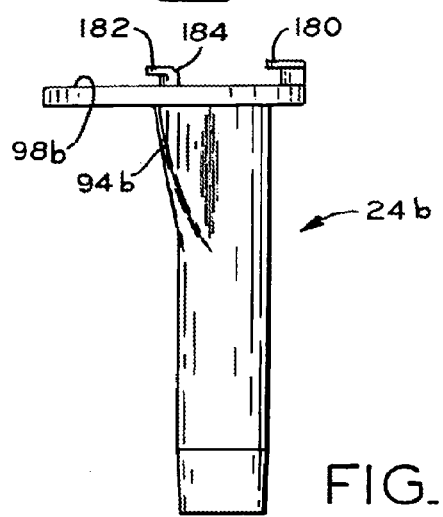
FIG_35
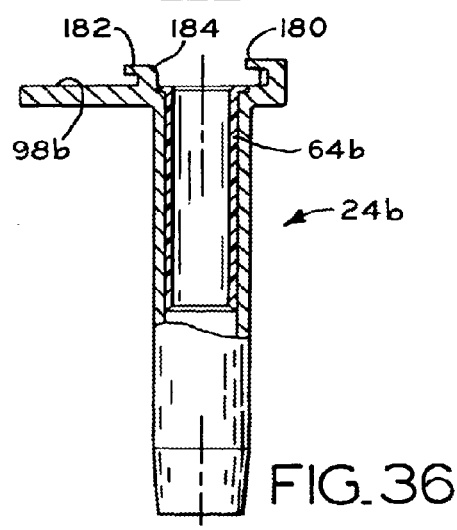
FIG_36

CONSTRAINED PROSTHETIC KNEE WITH ROTATING BEARING

CROSS-REFERENCE TO RELATED APPLICATIONS

This application is a continuation of U.S. patent application Ser. No. 12/790,181 filed May 28, 2010, which is a continuation of patent application Ser. No. 11/956,998 filed Dec. 14, 2007, which is a continuation of patent application Ser. No. 10/805,056 filed Mar. 19, 2004, which is a continuation of patent application Ser. No. 10/001,000 filed Nov. 2, 2001, now U.S. Pat. No. 6,719,800, which is a continuation-in-part of patent application Ser. No. 09/771,061 filed Jan. 29, 2001, now U.S. Pat. No. 6,485,519, the disclosures of which are expressly incorporated herein by reference.

BACKGROUND OF THE INVENTION

1. Field of the Invention

The present invention relates to prosthetic joints, and, more particularly to a constrained prosthetic knee having a modular hinge post and a rotating bearing.

2. Description of the Related Art

Generally, the knee is formed by the pair of condyles at the distal portion of the femur, the lower surfaces of which bear upon the correspondingly shaped proximal surface plateau of the tibia. The femur and tibia are connected by means of ligaments such as, the posterior cruciate ligament, the lateral collateral ligament, the medial collateral ligament, and the anterior cruciate ligament. These ligaments provide stability to the joint formed by the femur and tibia (i.e., the knee).

In a broad sense, prosthetic knee joints can be considered either constrained or unconstrained. For the purposes of this discussion, constrained prosthetic knees include femoral and tibial prosthetic components which are mechanically linked or constrained to each other by a hinge structure. An unconstrained prosthetic knee includes femoral and tibial components which are not mechanically linked. An unconstrained knee utilizes the patient's existing ligaments to provide joint stability. With this in mind, constrained prosthetic knees have particular applicability to cases in which a patient has experienced ligament loss and/or the existing ligaments do not provide adequate support and stability to the knee.

Tibial components of a prosthetic knee can be formed as a one-piece configuration in which the tibial tray forms the meniscal component of the prosthetic knee. Various other prosthetic knees utilize a modular meniscal component separate from the tibial component. Devices utilizing modular meniscal components include those in which the meniscal component (i.e., tibial bearing surface) is fixed to the tibial tray portion of the tibial component and is incapable of movement relative thereto. Alternative devices utilize a modular meniscal component capable of movement relative to the tibial tray. Devices in which relative rotational movement occurs between the meniscal component and the tibial component are typically referred to as rotating bearing knees. Rotating bearing knees thus allow movement between the bearing (i.e., meniscal component) and the tibial tray, as well as movement between the femoral component and the tibial bearing.

Constrained knees of the prior art include constructions in which a hinge post extension is first positioned within a tibial component (with an end protruding therefrom) and is thereafter connected to the femoral component by positioning the hinge post (rotatably attached to the femoral component) over the top of the protruding end of the hinge post extension and thereafter connecting the hinge post extension to the hinge post, e.g., by threading the hinge post extension into the hinge post. After making this connection, the meniscal component is thereafter slid into position between the femoral component and the tibial component. Meniscal components utilized with these prior art prosthetic knees are fixed to the tibial component.

The present invention is directed to a constrained knee prosthesis with a rotating bearing. The knee prosthesis of the present invention is structured to facilitate implantation thereof. The present invention is further directed to a prosthetic knee implant set having a plurality of matched modular hinge post and meniscal component pairs.

SUMMARY OF THE INVENTION

The present invention provides an improved constrained knee prosthesis having a cannulated hinge post facilitating implantation of the knee prosthesis in a relatively minimally invasive procedure. The prosthetic knee implant set of the current invention includes a separately packaged femoral component, a separately packaged tibial component, and a third package containing a hinge post extension and the meniscal component. Packaging the individual components of a knee prosthesis in this fashion insures that the appropriate hinge post extension is readily available. A bearing box is interposed between the hinge post and the femoral component. The bearing box includes a hyperextension stop which cooperates with the hinge post to prevent hyperextension of the knee prosthesis. Various structures are utilized to prevent the disengagement of the constrained knee prosthesis of the present invention.

A prosthetic knee constructed in accordance with the present invention includes a femoral component having a pair of condyler surfaces and a hinge post rotatably connected to the femoral component between the condyler surfaces. The hinge post is cannulated and accommodates insertion of a hinge post extension shaft therein. The hinge post and hinge post extension include cooperating locking tapers for locking the hinge post extension to the hinge post. Additionally, the hinge post includes internal threads so that a set screw may be threaded therein to further hold the hinge post extension in place. In one exemplary embodiment, the proximal end of the hinge post extension is threaded to facilitate locking the hinge post extension to the hinge post. The tibial component includes a hinge post extension aperture into which the hinge post extension is seated. The meniscal component similarly includes an aperture to accommodate the hinge post and hinge post extension. The meniscal component of the current invention is free to rotate about the hinge post during flexion and extension of the knee joint.

Having a cannulated hinge post through which a hinge post extension may be anteriorly positioned and secured advantageously allows for a relatively minimally invasive knee replacement procedure.

The present invention advantageously provides a constrained prosthetic knee having a rotating bearing flush with the condyler surfaces of the femoral component.

Another advantage of the present invention is the packaging of the prosthesis components and specifically the packaging of the appropriate hinge post extension together with a meniscal component.

BRIEF DESCRIPTION OF THE DRAWINGS

The above-mentioned and other features and advantages of this invention, and the manner of attaining of them, will become more apparent and the invention itself will be better understood by reference to the following description of an embodiment of the invention taken in conjunction with the accompanying drawings, wherein:

FIG. 2A is a perspective view of a hinge post extension of the present invention;

FIG. 13 is a cutaway, exploded view of an alternative embodiment of the knee prosthesis of the present invention;

FIG. 14 is a cutaway view of an assembled knee prosthesis in accordance with the embodiment illustrated in FIG. 13;

FIG. 15 is a fragmentary, cutaway view of an alternative embodiment of the hinge post extension and tibial bushing of the present invention;

FIG. 16 is a fragmentary, cutaway view of the embodiment of FIG. 15 illustrating insertion of the hinge post extension into the tibial bushing;

FIG. 17 is a fragmentary, cutaway view of the embodiment of FIG. 15 illustrating the hinge post extension fully inserted into the tibial bushing;

FIG. 18 is an exploded view of an alternative embodiment of the knee prosthesis of the current invention;

FIG. 19 is a sectional view of a meniscal component in accordance with an alternative embodiment of the present invention;

FIG. 20 is an elevational view of a hinge post in accordance with an alternative embodiment of the present invention;

FIG. 27 is a sectional view illustrating initial placement of a meniscal component of the present invention on a tibial component of the present invention;

FIGS. 28-30 are sectional views progressively illustrating placement of a meniscal component of the present invention on a tibial component of the present invention, whereby the meniscal component is operable to rotate relative to the tibial component when operably positioned thereon, but is constrained from movement in an axial direction relative to the tibial stem, i.e., the meniscal component will not lift away from the tibial component;

FIG. 31 is a top elevational view of a tibial component in accordance with the present invention;

FIGS. 32, 33, 34, and 35 are bottom, back, front, and side elevational views thereof, respectively; and FIG. 36 is a sectional view thereof.

Figure 1:
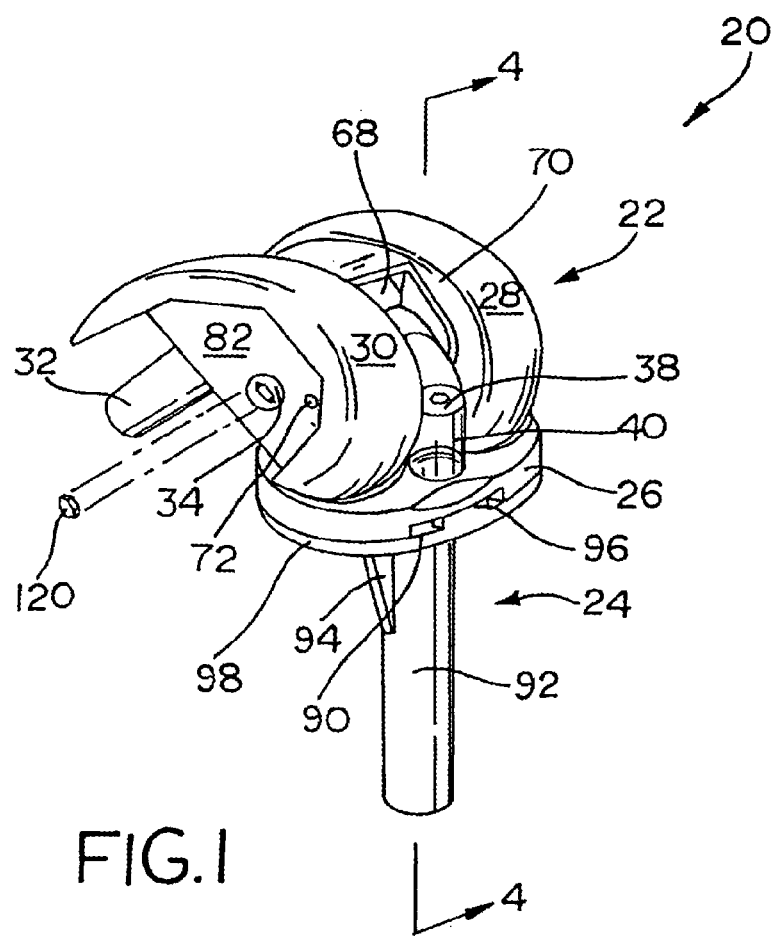
FIG. 1 is a perspective view of an assembled knee prosthesis in accordance with the present invention.

Corresponding reference characters indicate corresponding parts throughout the several views. Although the drawings represent embodiments of the invention, the drawings are not necessarily to scale and certain features may be exaggerated to better illustrate and explain the invention. The exemplifications set out herein illustrate embodiments of the invention, in alternative forms, and such exemplifications are not to be construed as limiting the scope of the invention in any manner.

DETAILED DESCRIPTION

Figure 2:
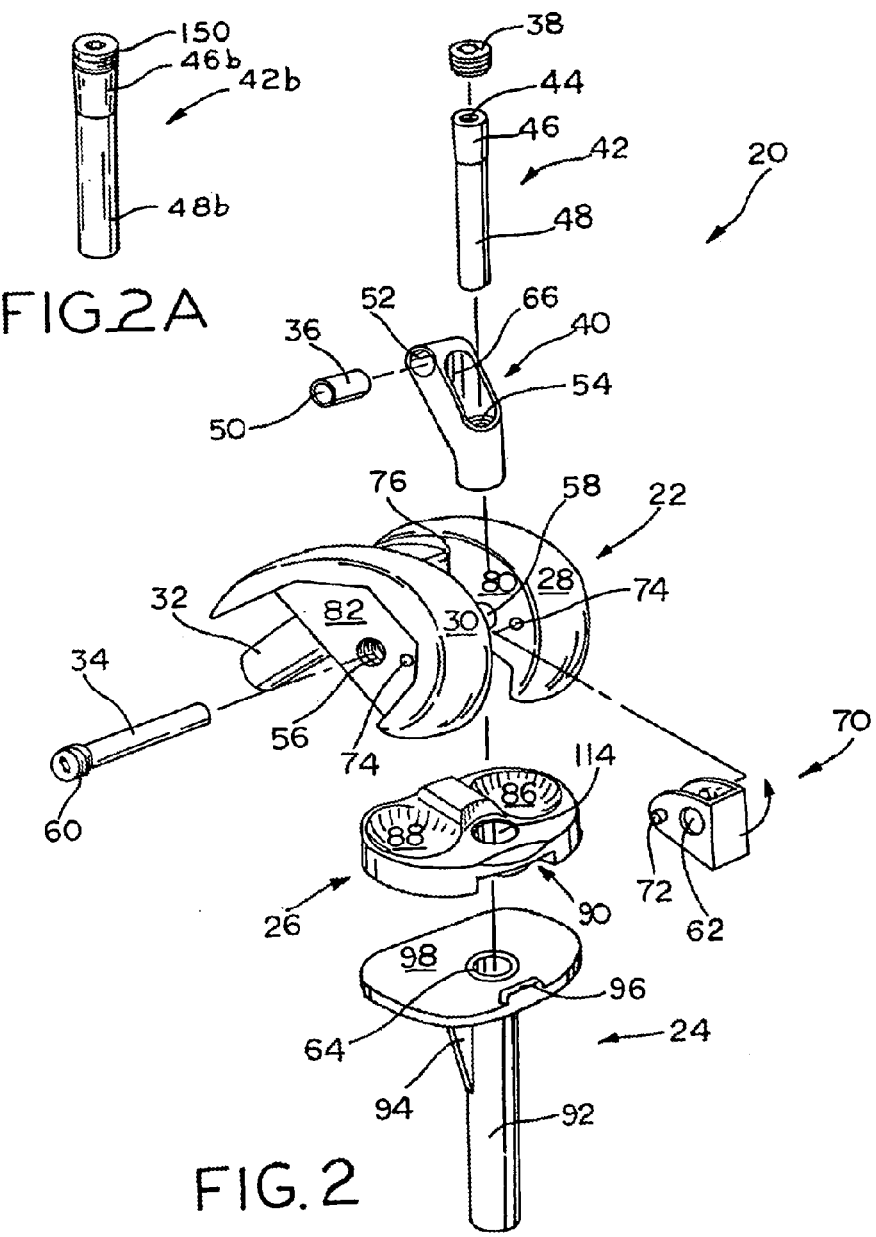
FIG. 2 is an exploded view thereof.
Figure 3:
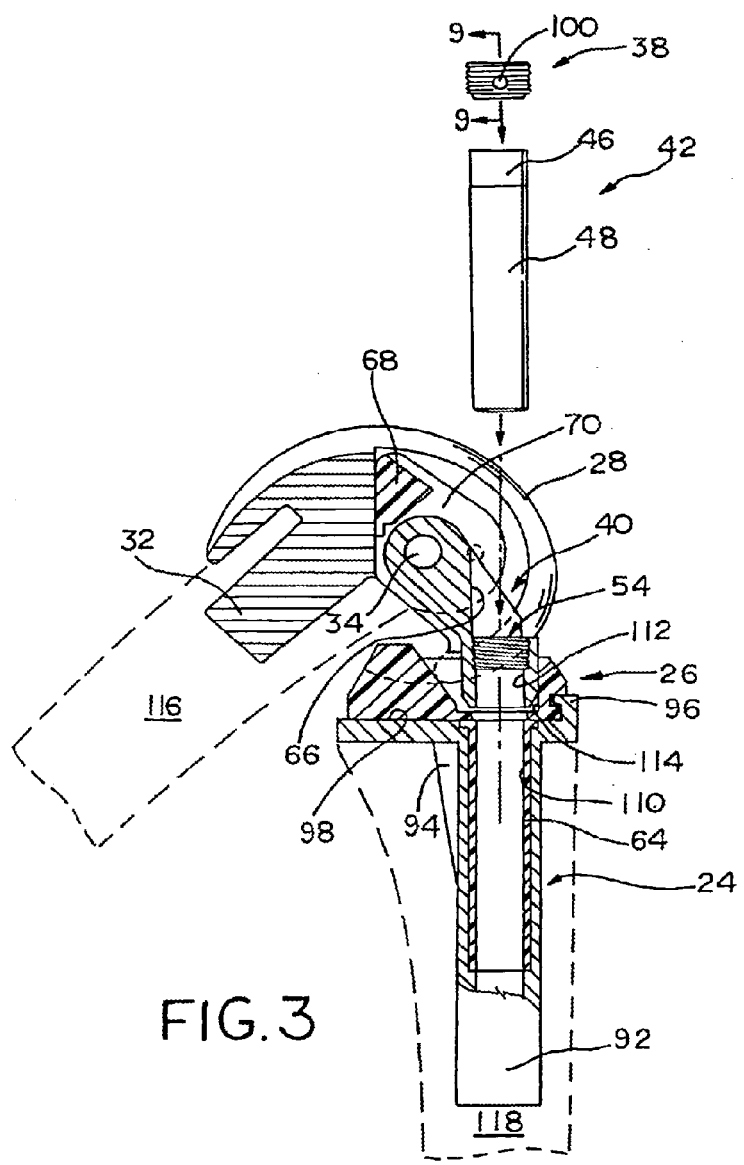
FIG. 3 is a cutaway, exploded view illustrating assembly of the knee prosthesis of the current invention including the anterior positioning of the hinge post extension into the hinge post.

Referring now to the drawings and particularly to FIG. 2, knee prosthesis 20 in accordance with the present invention is illustrated. Knee prosthesis 20 generally includes femoral component 22, tibial component 24, and meniscal component 26. Hinge post 40 is rotatably connected to femoral component 22 and includes elongate hinge post extension aperture 112 (FIGS. 3-6, 13, and 14). Elongate aperture 112 accommodates placement of hinge post extension 42 therein. Hinge post extension 42 thereafter traverses hinge post aperture 114 in meniscal component 26 and hinge post extension aperture 110 (FIGS. 3-6, 13 and 14) in tibial component 24. Elongate hinge post extension aperture 112 of hinge post 40 advantageously allows for anterior placement of hinge post extension 42 during surgical implantation of knee prosthesis 20 of the present invention.

Figure 4:
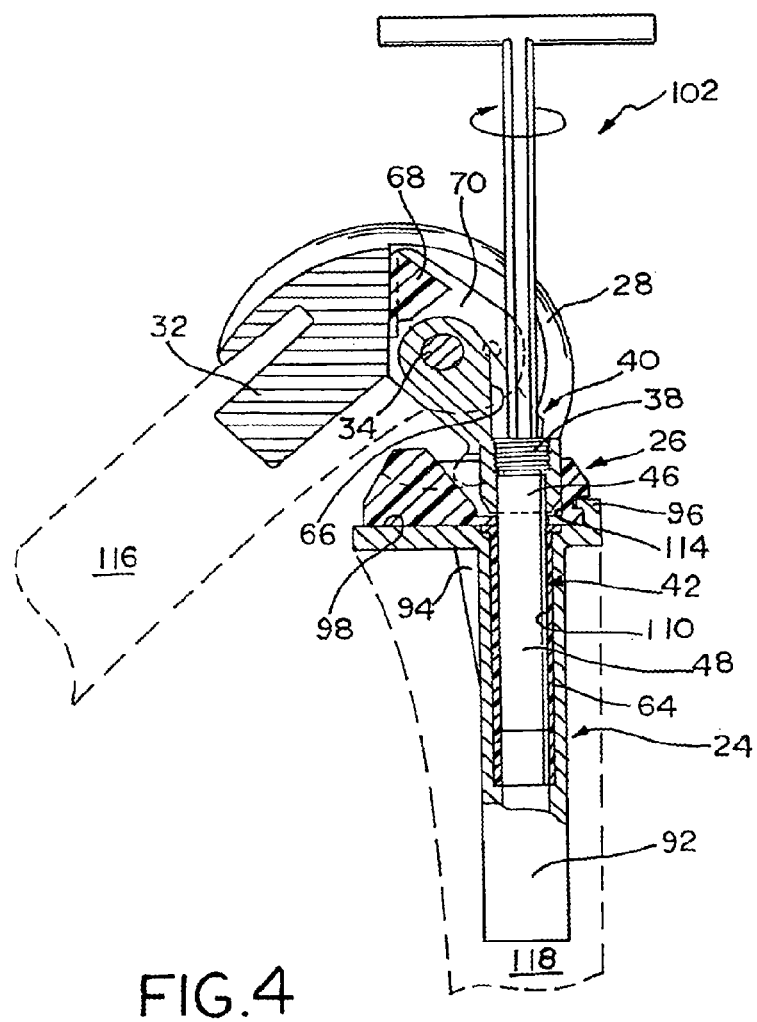
FIG. 4 is a cutaway view illustrating securement of the hinge plug (i.e., set screw) in the hinge post to facilitate locking of the hinge post extension therein.

As illustrated in FIG. 2, hinge post extension 42 includes locking taper 46 and cylindrical extension 48. Elongate hinge post extension aperture 112 includes a mating locking taper to cooperate with locking taper 46 and lock hinge post extension 42 to hinge post 40. After positioning hinge post extension 42 through apertures 112, 114, and 110, hinge plug 38 may be threaded into hinge plug threads 54 in elongate aperture 112 of hinge post 40 (FIG. 4). Hinge plug 38 abuts the end of hinge post extension 42 and thereby facilitates locking of morse taper 46 in elongate aperture 112. In one exemplary embodiment, locking taper 46 comprises a two degree locking taper. In an alternative embodiment, the hinge post extension includes integral threads to facilitate locking of the hinge post extension to the hinge post. As illustrated in FIG. 2A, hinge post extension 42B includes locking taper 46B as well as threaded proximal end 150. If hinge post extension 42B is utilized, hinge plug 38 is unnecessary. When prosthetic knee 20 is assembled as illustrated in FIG. 1, condyler bearing surfaces 28, 30 abut bearing surfaces 86, 88 (see, e.g., FIG. 2) of meniscal component 26.

Figure 9:
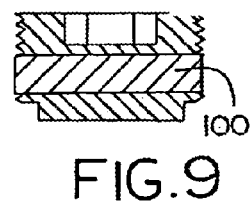
FIG. 9 is a sectional view of a hinge plug in accordance with the present invention.
Figure 7:
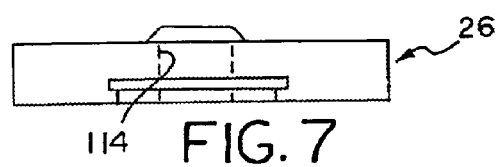
FIG. 7 is a front elevational view thereof.
Figure 8:
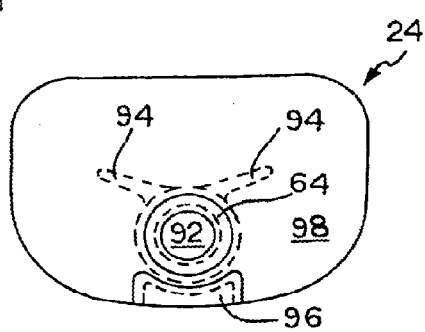
FIG. 8 is a top elevational view of a tibial component in accordance with the present invention.

Hinge post extension 42 is typically formed as a one-piece construction of an inert metal such, e.g., a cobalt-chromium alloy. Hinge post extension 42 may, however, be constructed of other bio-compatible metals or alloys, such as titanium. Throughout this document reference will be made to various components formed of a cobalt-chromium alloy. Any such component may also be constructed of other bio-compatible metals or alloys such as titanium, as is well-known. As illustrated in FIG. 4, hinge plug wrench 102 is utilized to thread hinge plug 38 into hinge plug threads 54 of hinge post 40. As illustrated in FIG. 9, hinge plug 38 includes locking material 100 to provide a locking connection between hinge plug 38 and hinge plug threads 54 in hinge post 40. Hinge plug 38 is, in one exemplary embodiment formed of a cobalt-chromium alloy. Locking material 100 comprises any suitable biocompatible polymer such as, e.g., ultra-high molecular weight polyethylene (UHMWPE).

As illustrated, e.g., in FIG. 2, femoral component 22 includes condyler bearing surfaces 28, 30 with bearing box wall 76 positioned therebetween. Femoral component 22 further includes external side walls 82, only one of which can be seen in FIG. 2. Condyler bearing surfaces 28, 30 are smooth and highly polished, generally spheroidally shaped and extend outwardly from external side walls 82, as is well known in the industry. Femoral component 22 further includes modular femoral stem 32 for insertion into femur 116 (FIGS. 3-5, 13, and 14), as is known in the art. Femoral component 22 further includes internal side walls 80, only one of which is illustrated in FIG. 2. Internal side walls 80 are substantially perpendicular to bearing box wall 76 and extend outwardly therefrom. Femoral component 22 is typically formed as a one-piece construction of an inert metal such as, e.g., a cobalt-chromium alloy.

Figure 10:
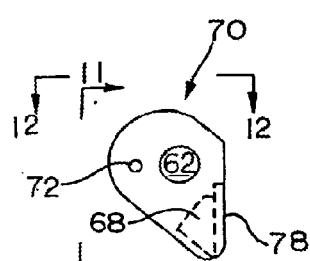
FIG. 10 is a side elevational view of a bearing box in accordance with the present invention.
Figure 11:
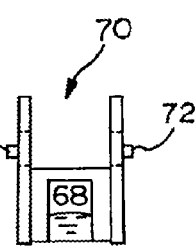
FIG. 11 is a front elevational view thereof.
Figure 12:
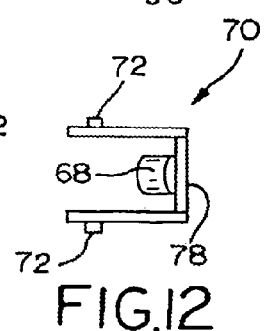
FIG. 12 is a top elevational view thereof.
Figure 21:
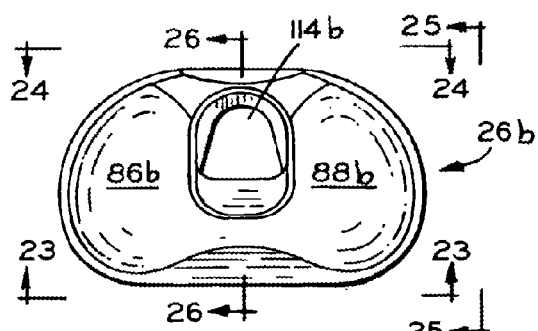
FIG. 21 is a top elevational view of a meniscal component in accordance with the present invention.

Bearing box 70 is designed for placement between condyler bearing surfaces 28, 30 of femoral component 22 as illustrated, e.g., in FIG. 1. Bearing box 70 is further illustrated in FIGS. 10-12 and includes affixing protrusions 72, hinge pin aperture 62, hyperextension stop 66, and anti-rotation surface 78. As illustrated in FIG. 2, femoral component 22 includes affixing protrusion apertures 74 sized to receive affixing protrusions 72. FIG. 1 illustrates bearing box 70 operably positioned on femoral component 22, with anti-rotation surface 78 flush with bearing box wall 76 of femoral component 22, and affixing protrusions 72 received in affixing protrusion apertures 74. The abutting relationship of anti-rotation surface 78 with bearing box wall 76 discourages rotation of bearing box 70 about the longitudinal axis of affixing protrusions 72. When bearing box 70 is positioned on femoral component 22, hinge pin apertures 62 of bearing box 70 align with threaded hinge pin aperture 56 and hinge pin aperture 58 of femoral component 22. Bearing box 70 can be formed of any suitable plastic, such as, e.g., UHMWPE.

Hinge post 40 is rotatably connected to femoral component 22 via hinge pin 34. Hinge post 40 is placed between opposing walls of bearing box 70 and is positioned so that hinge pin aperture 52 is aligned with apertures 56, 58, and 62. The opposing walls of bearing box 70 thus act as a bearing surface between hinge post 40 and internal side walls 80 of femoral component 22. Prior to placement of hinge post 40 between opposing walls of bearing box 70, hinge pin sleeve 36 is operably positioned within hinge pin aperture 52 of hinge post 40. Hinge post 40 is formed from a cobalt-chromium alloy, while hinge pin sleeve 36 is formed from a suitable plastic, such as, e.g., UHMWPE. Hinge pin sleeve 36 acts as a bearing between hinge pin aperture 52 of hinge post 40 and hinge pin 34. Accordingly, hinge pin sleeve 36 includes hinge pin aperture 50 sized to accommodate hinge pin 34. After positioning hinge post 40 between the opposing walls of bearing box 70, hinge pin 34 is positioned through apertures 56, 62, 50, and 58. Hinge pin threads 60 are thereafter threadedly engaged in the threads of threaded hinge pin aperture 56 until the head of hinge pin 34 is flush with external side wall 82.

As illustrated in FIG. 1, hinge pin plug 120 is positioned within the hexagonal indentation of hinge pin 34 after installation of hinge pin 34 as described above. When positioned within the hexagonal indentation of hinge pin 34, hinge pin plug 120 is flush with the head of hinge pin 34. In use, hinge pin plug 120 substantially prohibits the entry of foreign materials into the hexagonal indentation of hinge pin 34. For example, hinge pin plug 120 substantially prohibits bone growth into the hexagonal indentation of hinge pin 34, as well as prohibiting positioning of bone cement therein. The above-described connection of hinge post 40 to femoral component 22 is performed prior to implantation of femoral component 22. Femoral component 22 is packaged and sold with bearing box 70, hinge post 40, hinge pin sleeve 36, hinge pin 34, and hinge pin plug 120 preassembled as described above, with the assembly preferably occurring in the manufacturing environment.

Pre-assembly of hinge post 40 to femoral component 22 eliminates a number of meticulous assembly steps (many of which were performed during implantation) which were required with constrained knees of the prior art. Furthermore, the assembly of hinge post 40 and femoral component 22 as described above facilitates replacement of various portions of knee prosthesis 20. Specifically, the threaded connection of hinge pin 34 to femoral component 22 allows for removal and replacement of various components of knee prosthesis 20 including, e.g., bearing box 70, hinge pin sleeve 36, and hinge post 40.

In use, femoral bone stock may abut external side walls 82 of femoral component 22 and extend to the underside of condyler bearing surfaces 28, 30. To remove hinge pin 34, a hole saw is utilized to remove a relatively small portion of femoral bone stock to provide access to hinge pin 34. Advantageously, femoral component 22 does not require extensive removal of femoral bone stock for implantation thereof (since bone stock can extend to the underside of condylar bearing surfaces 28, 30), and, furthermore, does not require removal of femoral component 22 to effect replacement of, e.g., hinge post 40, bearing box 70, or hinge pin sleeve 36. Upon accessing hinge pin 34 (e.g., utilizing a hole saw as described above), hinge pin plug 120 is removed, e.g., with a scalpel and forceps to provide access to the hexagonal indentation of hinge pin 34 so that a hexagonal wrench may be inserted therein to unthread hinge pin 34 from femoral component 22.

Knee prosthesis 20 includes a pair of hyperextension stop mechanisms. The first hyperextension stop comprises a portion of condylar bearing surfaces 28, 30 of increased radius of curvature as compared to the remaining condylar bearing surface. At three degrees of hyperextension this portion of increased radius of curvature will contact meniscal component 26 and act to retard further hyperextension. If hyperextension continues, the area of increased radius of curvature will cause femoral component 22 to lift away from meniscal component 26. The second hyperextension stop mechanism functions at four degrees of hyperextension to prohibit further hyperextension of knee prosthesis 20. The second hyperextension stop mechanism comprises hyperextension stop surface 66 of hinge post 40 and hyperextension stop 68 of bearing box 70. Hyperextension stop surface 66 comprises the concave back wall of cannulated hinge post 40 as illustrated, e.g., in FIGS. 2 and 3. Hyperextension stop 68 of bearing box 70 comprises a protrusion extending from the back wall of bearing box 70 opposite anti-rotation surface 78. Hyperextension stop 68 includes a convex outer surface as illustrated, e.g., in FIG. 12. Hyperextension stop surface 66 of hinge post 40 cooperates with hyperextension stop 68 of bearing box 70 to provide a hyperextension stop for knee prosthesis 20. Concave hyperextension stop surface 66 becomes flush with the convex outer surface of hyperextension stop 68 of bearing box 70 at four degrees of hyperextension to prevent further hyperextension of knee prosthesis 20.

Tibial component 24 is depicted in FIGS. 1-5, 8, 13, and 14. As illustrated, e.g., in FIG. 2, tibial component 24 includes tibial tray 98 connected to tibial stem 92. Stabilizing ribs 94 stabilize tibial tray 98 relative to tibial stem 92 and impede rotation of tibial component 24 in tibia 118 (see, e.g., FIG. 3). In one exemplary embodiment, tibial component 24 is formed from a cobalt-chromium alloy. Tibial component 24 further includes tibial bushing 64 positioned within hinge post extension aperture 110. Tibial bushing 64 is formed of plastic, such as, e.g., UHMWPE and provides a bearing surface between hinge post extension 42 and hinge post extension aperture 110 of tibial component 24. As described above, meniscal component 26 comprises a rotating bearing, and, thus, hinge post extension 42 will rotate relative to tibial component 24. Tibial bushing 64 facilitates this rotation of hinge post extension 42.

Tibial component 24 further includes rotation protrusion 96. As illustrated, e.g., in FIG. 3, rotation protrusion 96 protrudes upwardly from tibial tray 98 of tibial component 24 and further extends in a plane substantially parallel to tibial tray 98. Rotation protrusion 96 cooperates with cutout 90 of meniscal component 26 to guide rotation of meniscal component 26 about hinge post extension 42, as further described hereinbelow. FIGS. 31-36 illustrate an alternative embodiment tibial component 24b. As illustrated, e.g., in FIG. 35, tibial component 24b includes a pair of rotation protrusions, i.e., anterior rotation protrusion 180, and posterior rotation protrusion 182. Rotation protrusions 180, 182 protrude upwardly from tibial tray 98b of tibial component 24b and further extend in a plane substantially parallel to tibial tray 98b. Rotation protrusions 180, 182 cooperate with anterior cutout 160, and posterior cutout 162 of meniscal component 26b, respectively (see, e.g., FIGS. 21-26) to guide rotation of meniscal component 26b about the hinge post extension, as further described hereinbelow.

One embodiment of meniscal component 26 is illustrated in FIGS. 1-7, 13, and 14. Meniscal component 26 is formed from a suitable plastic such as, e.g., UHMWPE and provides a rotating bearing surface between femoral component 22 and tibial component 24. Meniscal component 26 includes bearing surfaces 86, 88 which contact condylar bearing surfaces 28, 30 of femoral component 22 during movement of knee prosthesis 20. As described above, meniscal component 26 further includes hinge post aperture 114 accommodating passage of hinge post 40 and, consequently, hinge post extension 42 therethrough. Meniscal component 26 is operable to rotate about the longitudinal axis of hinge post extension 42 to form a rotating bearing.

Meniscal components of varying heights may be constructed in accordance with the present invention. In one advantageous aspect of the present invention, meniscal component 26 is packaged for sale and use together with hinge post extension 42 to facilitate component choice and, in one embodiment, to ensure proper extension of hinge post extension 42 into tibial component 24. The extension of hinge post extension 42 into tibial component 24 functions to prevent separation of knee prosthesis 20 after implantation thereof. As is known in the art, the femoral component of a knee prosthesis may, in some situations, move relative to and away from the tibial component in a direction parallel to the longitudinal axis of the hinge post extension. With this in mind, hinge post extension 42 is made to be of sufficient length to be retained within tibial component 24 even in situations in which femoral component 22 moves as described immediately supra. In one exemplary embodiment, hinge post extension 42 extends four centimeters into hinge post extension aperture 110 in tibial component 24.

Meniscal component 26 includes cutout 90 which cooperates with rotation protrusion 96 of tibial component 24 to guide rotation of meniscal component 26 and to resist lifting of meniscal component 26 from tibial tray 98 of tibial component 24. As illustrated, e.g., in FIG. 3, cutout 90 accommodates the portion (i.e., lip) of rotation protrusion 96 extending in a plane substantially parallel to the plane containing tibial tray 98, with a portion (i.e., lip) of meniscal component 26 being positioned between rotation protrusion 96 and tibial tray 98 in a direction substantially perpendicular to the plane containing tibial tray 98. This configuration functions to discourage displacement of meniscal component 26 away from tibial tray 98 in a direction parallel to the longitudinal axis of hinge post extension 42. Furthermore, rotation protrusion 96 acts against the back of cutout 90 to limit rotation of meniscal component 26 about the longitudinal axis of hinge post extension 42.

Figure 22:
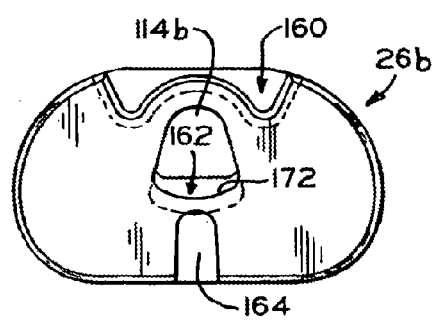
FIGS. 22, 23, 24, and 25 are bottom, back, front, and side elevational views thereof, respectfully.
Figure 23:
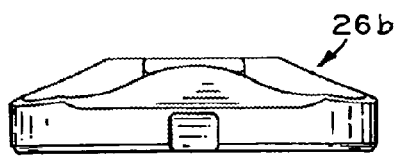
Figure 24:
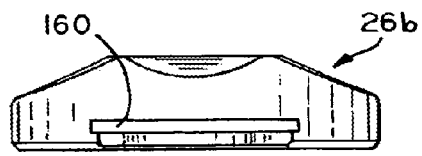
Figure 25:
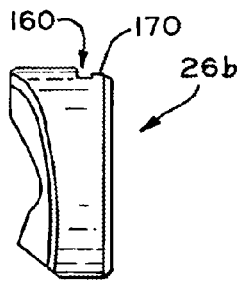
Figure 26:
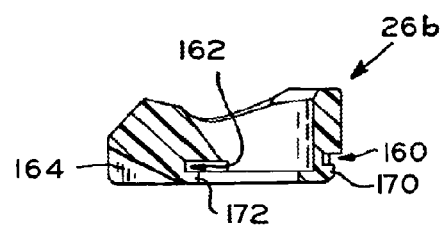
FIG. 26 is a sectional view thereof.

Meniscal component 26b illustrated in FIGS. 21-26, includes a pair of cutouts 160, 162 for cooperation with rotation protrusions 180, 182 of tibial component 24b (see, e.g., FIGS. 31-36) to guide rotation of meniscal component 26b and to resist lifting of meniscal component 26b from tibial tray 98b of tibial component 24b. As illustrated, e.g., in FIG. 26, meniscal component 26b includes anterior cutout 160 as well as posterior cutout 162, with anterior capture protrusion 170 and posterior capture protrusion 172 respectively extending therefrom. As illustrated in FIGS. 22 and 26, meniscal component 26b further includes channel 164 sized to accommodate posterior rotation protrusion 182 of tibial component 24b as will be further described hereinbelow.

As illustrated in FIGS. 27-30, tibial component 24b includes a pair of rotation protrusions, i.e., anterior rotation protrusion 180 and posterior rotation protrusion 182. As illustrated, e.g., in FIG. 30, anterior cutout 160 and posterior cutout 162 in meniscal component 26b respectively accommodate anterior capture protrusion 170 and posterior capture protrusion 172 formed in tibial component 26b. Specifically, cutouts 160, 162 accommodate the portion, i.e., lip of rotation protrusions 180, 182 extending in a plane substantially parallel to the plane containing tibial tray 98b, with a portion, i.e., lip of meniscal component 26b being positioned between the portions of rotation protrusions 180, 182 extending in a plane substantially parallel to the plane containing tibial tray 98, and tibial tray 98 when meniscal component 26b is operably positioned atop tribial tray 98b as illustrated, e.g., in FIG. 30. The cooperation of rotation protrusions 180, 182 with capture protrusions 170, 172, as illustrated, e.g., in FIG. 30 functions to discourage displacement of meniscal component 26b away from tibial tray 98b in a direction perpendicular to tibial tray 98b when the knee prosthesis of the current invention is operably assembled as illustrated, e.g., in FIG. 1. Furthermore, cutouts 160, 162 are sized whereby rotation protrusions 180, 182 cooperate therewith to limit rotation of meniscal component 26b about an axis generally perpendicular to tibial tray 98b of tibial component 24b. In one exemplary embodiment, meniscal component 26b is capable of a total of sixty degrees of rotation from one extreme to the other.

FIGS. 27-30 progressively illustrate movement of meniscal component 26b relative to tibial component 24b to achieve proper positioning of meniscal component 26b atop tibial tray 98b of meniscal component 24b. As illustrated in FIG. 27, posterior rotation protrusion 182 of tibial component 24b is positioned within channel 164 formed in meniscal component 26b, with meniscal component 26b resting atop rotation protrusion 180. Meniscal component 26b is thereafter moved posteriorly as illustrated in FIG. 28 until capture protrusions 170, 172 no longer rest atop rotation protrusions 180, 182, and meniscal component 26b is moved into contact with tibial tray 98b as illustrated in FIG. 29. Meniscal component 26b is subsequently moved anteriorly so that capture protrusions 170, 172 engage rotation protrusions 180, 182, respectively, to prevent movement of meniscal component 26b in a direction generally perpendicular to the plane containing tibial tray 98b, as illustrated in FIG. 30. As illustrated in FIG. 27, posterior rotation protrusion 82 includes bevel 184 to facilitate posterior movement of meniscal component 26b. Once meniscal component 26b is moved into the position illustrated in FIG. 30, hinge post extension 42 may be operably positioned within the tibial component as illustrated, e.g., in FIG. 4. Positioning of meniscal component 26b as described above in conjunction with FIGS. 27-30, may be effected in vivo with femoral component 22 in place, i.e., implanted in femur 116 as illustrated e.g., in FIG. 5. If meniscal component 26b is positioned with femoral component 22 in place, the steps described above will occur with condylar bearing surfaces 28-30 resting atop bearing surfaces 86b, 88d of meniscal component 26b, and with hinge post 40 positioned within hinge post aperture 114b of meniscal component 26b. As meniscal component 26b is moved relative to tibial component 24b as illustrated in FIGS. 27-30, hinge post 40 will rotate relative to femoral component 22 and move with meniscal component 26b.

Figure 5:
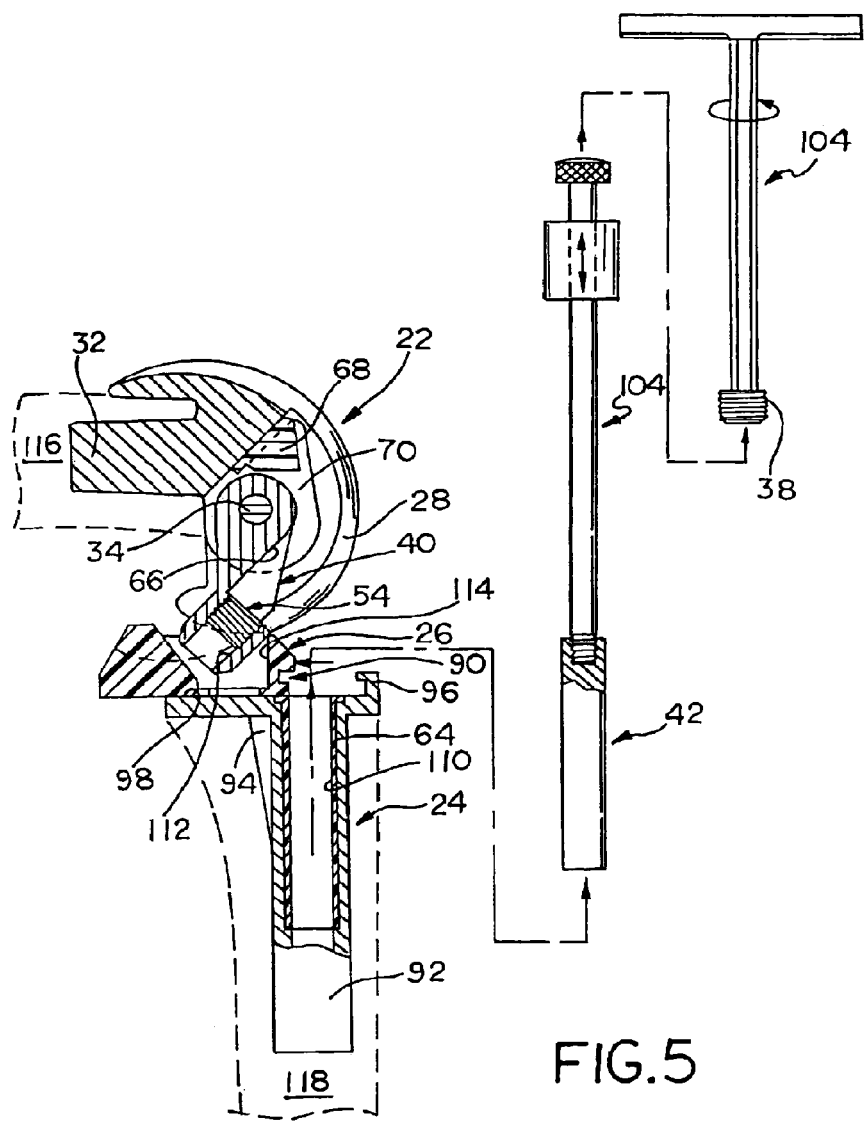
FIG. 5 is a cutaway, exploded view illustrating removal of the hinge post extension.
Figure 6:
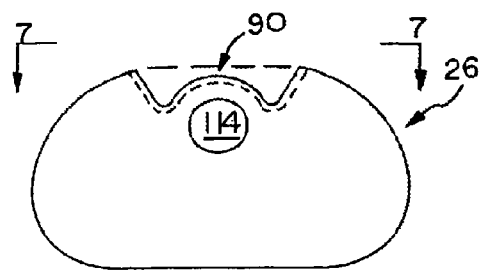
FIG. 6 is a bottom elevational view of the meniscal component of the present invention.

As illustrated in FIG. 5, meniscal component 26 may be slid out from between tibial component 24 and femoral component 22 when hinge post extension 42 has been removed from knee prosthesis 20. As illustrated, hinge post aperture 114 is sized to allow rotation of hinge post 40 so that meniscal component 26 may be slid out from its position between femoral component 22 and tibial component 24. Similarly, meniscal component 26b may be removed from position between tibial component 24b and the femoral component when hinge post extension 42 has been removed from knee prosthesis 20. If meniscal component 26b and tibial component 24b are utilized, meniscal component 26b is removed by reversing the steps utilized to position meniscal component 26b atop tibial component 24b described above in conjunction with FIGS. 27-30. This allows for replacement of an implanted meniscal component 26 without requiring removal of hinge post 40.

FIG. 5 illustrates removal of hinge post extension 42 to accommodate replacement of meniscal component 26. As illustrated, hinge plug wrench 102 engages hinge plug 38 for removal thereof. After removal of hinge plug 38, slap hammer 104 is threadedly engaged with threaded aperture 44 in hinge post extension 42. Slap hammer 104 may then be utilized to unlock the engagement of locking taper 46 in elongate hinge post extension aperture 112 so that hinge post extension 42 may be removed. If hinge post extension 42b illustrated in FIG. 2a is utilized, wrench 102 will be utilized to rotate hinge post extension 42b to cause threaded proximal end 150 thereof to retreat from hinge plug threads 54 in hinge post 40, thereby releasing engagement of locking taper 46b in elongate hinge post extension aperture 112 and allowing for removal of hinge post extension 42b.

FIGS. 13 and 14 illustrate a further alternative embodiment of the knee prosthesis of the current invention. This alternative embodiment utilizes hinge post extension 42a having locking taper 46a, cylindrical extension 48a, and flange 106. In this embodiment, a locking instrument may be utilized to apply force atop hinge post extension 42a so that locking taper 46a is seated in elongate hinge post extension aperture 112 and locked therein. Flange 106 may be utilized to facilitate removal of hinge post extension 42a. As illustrated in FIG. 13, set screw 108 may be utilized as a secondary lock for hinge post extension 42a.

FIGS. 15, 16 and 17 illustrate another alternative embodiment of the hinge post extension and tibial bushing of the present invention. In this embodiment, tibial component 24a includes annular tibial bushing expansion groove 122 formed in hinge post extension aperture 110. Tibial bushing 64a includes retaining flange 130 positioned within annular tibial bushing expansion groove 122. FIG. 15 illustrates insertion of cylindrical extension 48b of the hinge post extension into tibial bushing 64a positioned within tibial component 24a. As cylindrical extension 48b proceeds into tibial bushing 64a, bevel 126 contacts annular locking protrusion 128 of tibial bushing 64a and causes outward movement of retaining flange 130 as illustrated in FIG. 16 to allow cylindrical extension 48b to proceed to its seated position as illustrated in FIG. 17. Annular tibial bushing expansion groove 122 is sized to allow radial expansion of retaining flange 130 to accommodate placement of cylindrical extension 48b within tibial bushing 64a. In the fully seated position (FIG. 17) cylindrical extension 48b is locked in place by the engagement of annular locking protrusion 128 in annular locking groove 124. Furthermore, retaining flange 130 cooperates with annular tibial bushing expansion groove 122 to prohibit axial displacement of tibial bushing 64a and, consequently, cylindrical extension 48b. In this embodiment, the femoral component is retained in abutting relationship to the meniscal component and lift off of the femoral component is substantially prohibited. Tibial bushing 64a is, in one exemplary embodiment, formed of UHMWPE.

FIGS. 18 and 19 illustrate yet another alternative embodiment of the knee prosthesis of the current invention. In this embodiment, locking clip 134 is utilized to retain the position of hinge post 40b within hinge post aperture 114 of meniscal component 26a. Hinge post 40b is rotatably attached to femoral component 22 utilizing hinge pin 34 as described above. In this embodiment, hinge post 40b includes locking clip grooves 132, and meniscal component 26a includes locking clip apertures 136. Upon positioning of hinge post 40b within hinge post aperture 114, locking clip 134 is positioned as illustrated in FIG. 19 with the prongs of locking clip 134 being inserted into locking clip apertures 136 of meniscal component 26a. As illustrated in FIG. 19, locking clip 134 engages locking clip grooves 132 to retain hinge post 40b within hinge post aperture 114 of meniscal component 26a. In this embodiment, lift off of femoral component 22 is prohibited by the engagement of hinge post 40b with meniscal component 26a. This embodiment of the knee prosthesis of the current invention may further utilize a meniscal component cutout together with a rotation protrusion on the tibial component to resist lifting of the meniscal component from the tibial tray as described above.

FIG. 20 illustrates a further alternative embodiment of the hinge post of the present invention. Hinge post 40c illustrated in FIG. 20 includes reinforcing material 138 to strengthen hinge post 40c.

While this invention has been described as a prosthetic knee with a rotating bearing, it is contemplated that various aspects of the present invention, including, e.g., the cannulated hinge post will be utilized with a prosthetic knee having a fixed bearing.

While this invention has been described as having exemplary designs, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:
1. A prosthetic knee assembly, comprising:
a femoral component body that includes a first internal side wall opposing a second internal side wall;
a hinge pin having a longitudinal hinge pin axis;
a hinge post positioned between the first internal side wall and the second internal side wall of the femoral compo- nent body, said hinge post rotatably connected to said femoral component body with said hinge pin passing through a hinge pin aperture in said hinge post so that rotation of said hinge post relative to said femoral component body is defined about the longitudinal hinge pin axis, said hinge post providing a hinge post extension aperture extending through the hinge post along a longitudinal hinge post axis that is non-intersecting with and transverse to said longitudinal hinge pin axis; and a hinge post extension received in the hinge post extension aperture and removeably locked to the hinge post.

2. The prosthetic knee assembly of claim 1, further comprising a tibial component that includes an elongate aperture for receiving a distal section of said hinge post extension, wherein, when the femoral component body is attached to a femur and the tibial component is attached to a tibia opposite the femur, the distal section of the hinge post extension is insertable into the elongate aperture of the tibial component from an anterior surgical approach.

3. The prosthetic knee assembly of claim 2, wherein the hinge post extension being removeably locked to the hinge post includes a threaded connection between a proximal portion of the hinge post extension and an inner wall of the hinge post extension aperture.

4. The prosthetic knee assembly of claim 3, further comprising a bearing member that provides a first bearing side wall situated between the hinge post and the first internal side wall of the femoral component body and a second bearing side wall situated between the hinge post and the second internal side wall of the femoral component body.

5. The prosthetic knee assembly of claim 1, further comprising a plug member advanceable within said hinge post extension aperture to facilitate locking the hinge post extension to the hinge post, wherein said plug member is threadably advanceable along said longitudinal hinge post axis.

6. A prosthetic knee, comprising:
a femoral component including a condylar bearing surface;
a hinge post rotatably connected to said femoral component about a rotational axis, said hinge post providing a hinge post extension aperture extending through the hinge post along a longitudinal hinge post axis that is non-intersecting with and transverse to said rotational axis;
a tibial component;
a hinge post extension receivable in the hinge post extension aperture for connection to the hinge post, said hinge post extension receivable in an elongate aperture of the tibial component; and
a meniscal component positionable between said femoral component and said tibial component so as to provide a cooperative bearing surface facing said condylar bearing surface of said femoral component, said meniscal component including a hinge post aperture in which said hinge post can be positioned,
wherein, when the femoral component is attached to a femur and the tibial component is attached to a tibia opposite the femur, said hinge post can be rotated about said rotational axis and said meniscal component can be inserted between the femoral component and the tibial component.

7. The prosthetic knee assembly of claim 6, wherein the hinge post extension includes a threaded proximal section for threadably engaging an inner wall of the hinge post extension aperture.

8. The prosthetic knee assembly of claim 7, wherein, when the femoral component is attached to a femur and the tibial component is attached to a tibia opposite the femur, a distal end of the hinge post extension can be passed through the hinge post extension aperture and into the elongate aperture of the tibial component from an anterior surgical approach.

9. The prosthetic knee of claim 6, wherein said tibial component includes a tibial tray with a protrusion protruding from the tibial tray, the protrusion cooperable with a cut-out in the meniscal component.

10. A prosthetic knee assembly, comprising:
a femoral component body that includes a first internal side wall opposing a second internal side wall;
a hinge pin having a longitudinal hinge pin axis;
a hinge post positioned between the first internal side wall and the second internal side wall of the femoral component body, said hinge post rotatably connected to said femoral component body with said hinge pin fixed to said femoral component body and passing through a hinge pin aperture in said hinge post so that rotation of said hinge post relative to said femoral component body is defined about the longitudinal hinge pin axis, said hinge post including a longitudinal hinge post axis that is transverse to said longitudinal hinge pin axis and providing a hinge post extension aperture along said longitudinal hinge post axis, said hinge post extension aperture providing a first exterior opening in said hinge post and a second exterior opening in said hinge post, said first exterior opening and said second exterior opening spaced from one another along said longitudinal hinge post axis; and
a hinge post extension received in said hinge post extension aperture and removeably locked to the hinge post.

11. The prosthetic knee assembly of claim 10, wherein, when the femoral component body is attached to a femur, the hinge post extension can be unlocked from the hinge post and removed from the hinge post extension aperture from an anterior surgical approach.

12. The prosthetic knee assembly of claim 10, wherein the hinge post extension includes a distal end located outside the hinge post extension aperture and a threaded proximal portion located inside the hinge post extension aperture and threadably engaging an inner wall of the hinge post extension aperture.

13. The prosthetic knee assembly of claim 10, further comprising a tibial component that includes an elongate aperture for receiving the distal end of said hinge post extension.

14. The prosthetic knee of claim 13, further comprising a meniscal component positionable between said femoral component body and said tibial component, wherein said tibial component includes a tibial tray with a protrusion protruding from the tibial tray, the protrusion cooperable with a cut-out in the meniscal component.

15. A prosthetic knee, comprising:
a femoral component including a condylar bearing surface;
a hinge post rotatably connected to said femoral component about a rotational axis, said hinge post providing a hinge post extension aperture extending through the hinge post along a longitudinal hinge post axis that is non-intersecting with and transverse to said rotational axis;
a tibial component;
a meniscal component positionable between said femoral component and said tibial component so as to provide a cooperative bearing surface facing said condylar bearing surface of said femoral component, said meniscal component including a hinge post aperture in which said hinge post can be positioned; and
a hinge post extension receivable in an elongate aperture of the tibial component for connection to the hinge post.

16. The prosthetic knee assembly of claim 15, wherein the hinge post extension includes a threaded proximal section.

17. The prosthetic knee assembly of claim 16, wherein the threaded proximal section is threadably engageable with an inner wall of the hinge post extension aperture.

18. The prosthetic knee assembly of claim 17, wherein, when the femoral component is attached to a femur and the tibial component is attached to a tibia opposite the femur, a distal end of the hinge post extension can be passed through the hinge post extension aperture and into the elongate aperture of the tibial component from an anterior surgical approach.

19. The prosthetic knee assembly of claim 17, wherein, when the femoral component is attached to a femur and the tibial component is attached to a tibia opposite the femur, the hinge post extension can be locked and unlocked from the hinge post from an anterior surgical approach.

20. The prosthetic knee assembly of claim 15, wherein the hinge post extension can be removeably locked to the hinge post so as to provide a distal shaft portion of the hinge post extension located outside the hinge post extension aperture and a threaded proximal section of the hinge post extension located inside the hinge post extension aperture and threadably engaging an inner wall of the hinge post extension aperture.

21. The prosthetic knee of claim 15, wherein said hinge post can be rotated about said rotational axis and said meniscal component can be inserted between the femoral component and the tibial component from an anterior surgical approach when the femoral component is attached to a femur and the tibial component is attached to a tibia opposite the femur.

22. The prosthetic knee of claim 15, wherein said tibial component includes a tibial tray with a protrusion protruding from the tibial tray, the protrusion cooperable with a cut-out in the meniscal component.

23. The prosthetic knee assembly of claim 15, further comprising a bearing member that provides a first bearing side wall situated between the hinge post and a first internal side wall of the femoral component and a second bearing side wall situated between the hinge post and a second internal side wall of the femoral component.

24. A prosthetic knee assembly, comprising:
a femoral component body that includes a first internal side wall opposing a second internal side wall;
a hinge post positioned between the first internal side wall and the second internal side wall of the femoral component body, said hinge post rotatably connected to said femoral component body about a rotational axis, said hinge post including a longitudinal hinge post axis that is non-intersecting with and transverse to said rotational axis, said hinge post providing a hinge post extension aperture which provides a first exterior opening in said hinge post and a second exterior opening in said hinge post, said first exterior opening and said second exterior opening spaced from one another along said longitudinal hinge post axis; and
a hinge post extension received in the hinge post extension aperture and removeably locked to the hinge post.

25. The prosthetic knee assembly of claim 24, wherein the hinge post extension includes a distal end located outside the hinge post extension aperture and a threaded proximal portion located inside the hinge post extension aperture and threadably engaging an inner wall of the hinge post extension aperture.

26. The prosthetic knee assembly of claim 25, wherein the distal end of the hinge post extension is passable entirely through the hinge post extension aperture from the first exterior opening to the second exterior opening when receiving the hinge post extension in the hinge post extension aperture.

27. The prosthetic knee assembly of claim 26, wherein the threaded proximal portion of the hinge post extension is advanceable along the inner wall of the hinge post extension aperture in a direction from the first exterior opening toward the second exterior opening when removeably locking the hinge post extension to the hinge post.

28. The prosthetic knee assembly of claim 24 further comprising a tibial component, with a distal section of said hinge post extension receivable in an elongate aperture of the tibial component.

29. The prosthetic knee assembly of claim 28 further comprising a tibial bushing received in the elongate aperture of the tibial component, said tibial bushing including a first flange abutting a first transverse wall in the elongate aperture of the tibial component for retaining said tibial bushing in the elongate aperture of the tibial component, said hinge post extension including a second flange abutting a second transverse wall in tibial bushing for retaining said hinge post extension in the tibial bushing.

30. The prosthetic knee assembly of claim 28 further comprising a meniscal component positionable between said femoral component body and said tibial component.

31. The prosthetic knee assembly of claim 30, wherein said tibial component includes a tibial tray with a protrusion protruding from the tibial tray, the protrusion cooperable with a cut-out in the meniscal component.

32. The prosthetic knee assembly of claim 24, wherein the hinge post extension is formed as a one-piece construction.

33. The prosthetic knee assembly of claim 24 including a threaded connection locking the hinge post extension to the hinge post.

34. The prosthetic knee assembly of claim 33, wherein a threaded member is seated in the hinge post extension aperture to facilitate locking the hinge post extension to the hinge post.

35. The prosthetic knee assembly of claim 24, further comprising a bearing member that provides a first bearing side wall situated between the hinge post and the first internal side wall of the femoral component body and a second bearing side wall situated between the hinge post and the second internal side wall of the femoral component body.

36. The prosthetic knee assembly of claim 35, wherein the first bearing side wall includes a portion received in a side wall aperture in the first internal side wall of the femoral component body, and wherein the second bearing side wall includes a portion received in a side wall aperture in the second internal side wall of the femoral component body.

37. The prosthetic knee assembly of claim 35, wherein the first bearing side wall includes a side protrusion received in a side wall aperture in the first internal side wall of the femoral component body, and wherein the second bearing side wall includes a side protrusion received in a side wall aperture in the second internal side wall of the femoral component body.

38. The prosthetic knee assembly of claim 35, wherein said bearing member includes a curved back wall.

39. The prosthetic knee assembly of claim 38, wherein said curved back wall of the bearing member is cooperable in a convexo-concave fashion with a curvature in a back wall of the hinge post.

40. The prosthetic knee assembly of claim 24, wherein, when the femoral component body is attached to a femur, from an anterior surgical approach the hinge post extension can be unlocked from the hinge post and removed from the hinge post extension aperture to be replaced by a replacement hinge post extension.

41. A prosthetic knee, comprising:
a femoral component that includes a condylar bearing surface and provides a first internal side wall opposing a second internal side wall;
a hinge post positioned between the first internal side wall and the second internal side wall of the femoral component, said hinge post rotatably connected to said femoral component about a rotational axis, said hinge post including a longitudinal hinge post axis that is non-intersecting with and transverse to said rotational axis, said hinge post providing a hinge post extension aperture which provides a first exterior opening in said hinge post and a second exterior opening in said hinge post, said first exterior opening and said second exterior opening spaced from one another along said longitudinal hinge post axis;
a tibial component;
a meniscal component positionable between said femoral component and said tibial component so as to provide a cooperative bearing surface facing the condylar bearing surface of said femoral component, said meniscal component including a hinge post aperture in which said hinge post can be rotatably received; and
a hinge post extension including a distal end and a threaded proximal portion, wherein said distal end can be passed entirely through the hinge post extension aperture from the first exterior opening to the second exterior opening so as to extend a distance from the hinge post for being received in an elongate aperture of the tibial component, and wherein said threaded proximal portion can be threadably advanced along the hinge post extension aperture in a direction from the first exterior opening toward the second exterior opening for removeably locking the hinge post extension to the hinge post.

42. The prosthetic knee of claim 41, wherein, when the femoral component is attached to a femur and the tibial component is attached to a tibia opposite the femur, (a) said meniscal component can be inserted between the femoral component and the tibial component from an anterior surgical approach; (b) said hinge post can be rotated about said rotational axis and received in the hinge post aperture of the meniscal component, wherein the first exterior opening in the hinge post is exposed for receiving the hinge post extension; (c) the distal end of the hinge post extension can be passed entirely through said hinge post extension aperture by entering the hinge post extension aperture through said first exterior opening and exiting the hinge post extension aperture through the second exterior opening; (d) the distal end of the hinge post extension can be received in the elongate aperture of the tibial component; and (e) the threaded proximal portion of the hinge post extension can be threadably advanced along the hinge post extension aperture in a direction from the first exterior opening toward the second exterior opening to removeably lock the hinge post extension to the hinge post.

* * * * *